(12) United States Patent
Johnson

(10) Patent No.: US 7,204,252 B2
(45) Date of Patent: Apr. 17, 2007

(54) SURFACE ENERGY ASSISTED FLUID TRANSPORT SYSTEM

(75) Inventor: Roger N. Johnson, Mercer Island, WA (US)

(73) Assignee: Eidon, LLC, Long Lake, MN (US)

( * ) Notice: Subject to any disclaimer, the term of this patent is extended or adjusted under 35 U.S.C. 154(b) by 502 days.

(21) Appl. No.: 10/321,790

(22) Filed: Dec. 16, 2002

(65) Prior Publication Data

US 2003/0145860 A1    Aug. 7, 2003

Related U.S. Application Data

(60) Provisional application No. 60/343,495, filed on Dec. 21, 2001.

(51) Int. Cl.
*A61M 16/00* (2006.01)

(52) U.S. Cl. ............................. 128/207.15; 128/207.14

(58) Field of Classification Search ........... 128/207.14, 128/207.15, 207.16, 207.18, 200.26
See application file for complete search history.

(56) References Cited

U.S. PATENT DOCUMENTS

| | | | | |
|---|---|---|---|---|
| 3,591,319 | A | * 7/1971 | Shlisky | ........................ 417/477 |
| 3,971,385 | A | 7/1976 | Corbett | |
| 4,091,816 | A | 5/1978 | Elam | |
| 4,278,081 | A | 7/1981 | Jones | |
| 4,305,392 | A | 12/1981 | Chester | ........................ 128/276 |
| 4,327,721 | A | 5/1982 | Goldin et al. | |
| 4,341,210 | A | 7/1982 | Elam | |
| 4,502,482 | A | 3/1985 | DeLuccia et al. | ...... 128/207.15 |
| 4,511,354 | A | * 4/1985 | Sterling | ........................ 604/98 |
| 4,584,998 | A | 4/1986 | McGrail | |
| 4,607,635 | A | 8/1986 | Heyden | |
| 4,632,108 | A | 12/1986 | Geil | |
| 4,637,389 | A | * 1/1987 | Heyden | ........................ 128/207.15 |
| 4,653,987 | A | * 3/1987 | Tsuji | ........................ 417/360 |
| 4,688,568 | A | 8/1987 | Frass et al. | |
| 4,700,700 | A | 10/1987 | Eliachar | |
| 4,762,125 | A | 8/1988 | Leiman et al. | |

(Continued)

FOREIGN PATENT DOCUMENTS

EP      0808636      11/1997

(Continued)

OTHER PUBLICATIONS

"PCT Search Report for PCT/US 02/40376", *Applicant's Ref. No. 1682.001WO1*, Filed Dec. 18, 2002,(Apr. 16, 2003),10 pages.

*Primary Examiner*—Henry Bennett
*Assistant Examiner*—D. Doster-Greene
(74) *Attorney, Agent, or Firm*—Popovich, Wiles & O'Connell, P.A.

(57) ABSTRACT

A system, device or method uses surface energy to assist in fluid transport or separation. One example includes removing mucus from a subject's lungs during mechanical ventilation of the subject using a tracheal tube. At least one wicking fluid pickup port is located more distal or more proximal than a sealing device between the tracheal tube and the trachea. Surface energy assists in introducing mucus into the port. A peristalsis or other pump is used to remove from the subject the wicked-in liquid. Ventilation is not impaired by the mucus removal.

16 Claims, 15 Drawing Sheets

U.S. PATENT DOCUMENTS

| | | | |
|---|---|---|---|
| 4,819,619 A * | 4/1989 | Augustine | 128/200.26 |
| 4,840,173 A | 6/1989 | Porter, III | |
| 4,886,059 A | 12/1989 | Weber | |
| 4,976,261 A | 12/1990 | Gluck et al. | |
| 4,979,505 A | 12/1990 | Cox | |
| 4,995,388 A | 2/1991 | Brain | |
| 5,033,466 A | 7/1991 | Weymuller, Jr. | |
| 5,067,497 A | 11/1991 | Greear et al. | |
| 5,076,268 A | 12/1991 | Weber | |
| 5,116,305 A | 5/1992 | Milder et al. | |
| 5,143,062 A | 9/1992 | Peckham | |
| 5,201,310 A | 4/1993 | Turnbull | |
| 5,241,956 A | 9/1993 | Brain | |
| 5,311,864 A | 5/1994 | Huerta | |
| 5,372,131 A | 12/1994 | Heinen, Jr. | |
| 5,501,215 A | 3/1996 | Huerta | |
| 5,520,175 A | 5/1996 | Fry | |
| 5,582,167 A | 12/1996 | Joseph | |
| 5,653,229 A | 8/1997 | Greenberg | |
| 5,697,365 A | 12/1997 | Pell | 128/207.15 |
| 5,725,510 A | 3/1998 | Hartmann et al. | |
| 5,765,559 A | 6/1998 | Kim | |
| 5,819,723 A | 10/1998 | Joseph | |
| 5,832,920 A | 11/1998 | Field | |
| 5,937,861 A | 8/1999 | Augustine | |
| 6,062,223 A | 5/2000 | Palazzo et al. | |
| 6,103,181 A * | 8/2000 | Berger | 264/555 |
| 6,152,136 A | 11/2000 | Pagan | |
| 6,210,083 B1 | 4/2001 | Kammermeier et al. | 408/1 R |
| 6,460,540 B1 | 10/2002 | Klepper | |
| 6,543,451 B1 | 4/2003 | Crump et al. | 128/207.14 |
| 6,802,317 B2 | 10/2004 | Göbel | |
| 2004/0255951 A1 | 12/2004 | Grey | |

FOREIGN PATENT DOCUMENTS

JP            10131861 A *    5/1998

* cited by examiner

SURFACE ENERGY ASSISTED FLUID TRANSPORT SYSTEM

CROSS-REFERENCE TO RELATED APPLICATIONS

This patent application claims the benefit of priority, under 35 U.S.C. Section 119(e), to Roger N. Johnson U.S. Provisional Patent Application Ser. No. 60/343,495, entitled "SURFACE ENERGY ASSISTED FLUID TRANSPORT SYSTEM," filed on Dec. 21, 2001.

FIELD OF THE INVENTION

This document relates generally to fluid transportation, and particularly, but not by way of limitation, to surface energy assisted systems and methods for transporting fluids.

BACKGROUND

When a patient is unable to adequately breathe independently, an external mechanical ventilator may be used to provide temporary or permanent breathing support. The ventilator pumps air into and out of the subject's lungs such as, for example, though an endotracheal (ET) or other tracheal tube. In one example, a distal portion of the tracheal tube is introduced into the subject's trachea (windpipe) through an incision made in the subject's throat. A proximal portion of the tracheal tube is connected to the ventilator. An inflatable cuff near the distal end of the tracheal tube is inflated to completely occupy the intratracheal region surrounding the tracheal tube. This creates a seal that prevents airflow through the trachea other than through the tracheal tube, so that the ventilator can provide the subject with breathing support through the tracheal tube. In another example, the tracheal tube is inserted via the subject's mouth, rather than into an incision in the subject's throat.

However, normal lungs continuously secrete mucus that is sticky enough to trap foreign particles. In the absence of the ventilator and tracheal tube, such secreted mucus would be carried up the windpipe to the throat by the action of cilia, such that the patient may then swallow the mucus. When damage or disease disables this mechanism, or reduces its ability to move the required volume of mucus, there exists a risk of the lungs drowning in fluid. In addition, certain medical procedures may disrupt such normal mucus transport. For example, the inflatable cuff at the distal end of a tracheal tube inserted into a person on a ventilator will block the normal flow of the lung-cleansing mucus.

One technique for removing accumulated fluid from the lungs includes interrupting the patient's ventilation by disconnecting the proximal end of the tracheal tube from the ventilator. A suction tube is then inserted through the tracheal tube beyond the cuff at its distal end. By applying an airflow-creating vacuum to the proximal end of the suction tube, fluid is removed from the lungs. However, such an airflow-creating vacuum has a limited capability to lift fluid through a small diameter tube against the force of gravity, to remove the fluid from the lungs. Moreover, this procedure must be repeated often enough (e.g., every 0.25 to 8 hours). Otherwise, the mucus may accumulate or dry, which, in turn, may make its removal more difficult. Each occurrence of such airflow suctioning interrupts the breathing assistance provided by the ventilator. Moreover, such airflow suctioning risks damage to the windpipe walls. It also creates a risk of infection to both the patient and the caregiver, who may come in contact with the extracted fluids or the air used to suction the fluid. The risk of infection is exacerbated because the suction tube is typically re-used despite its contamination and direct connection to a waste container that stores the suctioned fluid. Moreover, frequent intervention by a caregiver is aggravating to the patient, and may cause considerable resulting anxiety. Such frequent intervention by a caregiver is also costly. In addition, the caregiver must be well-trained to reduce the risks of damage or infection presented by such repeated suctioning. Among other things, the present inventors have recognized that continuous airflow-assisted suctioning, however, would likely interfere with the patient's breathing because of the airflow required to vacuum the fluid from the lungs. For these and other reasons, the present inventors have recognized an unmet need for improved fluid transportation techniques, such as for removing mucus from a patient's lungs that are being mechanically ventilated, or for otherwise removing bodily fluids from a patient.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

DETAILED DESCRIPTION

In the following detailed description, reference is made to the accompanying drawings that form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the scope of the present invention. The following detailed description is, therefore, not to be taken in a limiting sense, and the scope of the present invention is defined by the appended claims and their equivalents.

In this document, the terms "a" or "an" are used, as is common in patent documents, to include one or more than one. Furthermore, all publications, patents, and patent documents referred to in this document are incorporated by reference herein in their entirety, as though individually incorporated by reference. In the event of inconsistent usages between this documents and those documents so incorporated by reference, the usage in the incorporated reference(s) should be considered supplementary to that of this document; for irreconciliable inconsistencies, the usage in this document controls.

Figure 1:
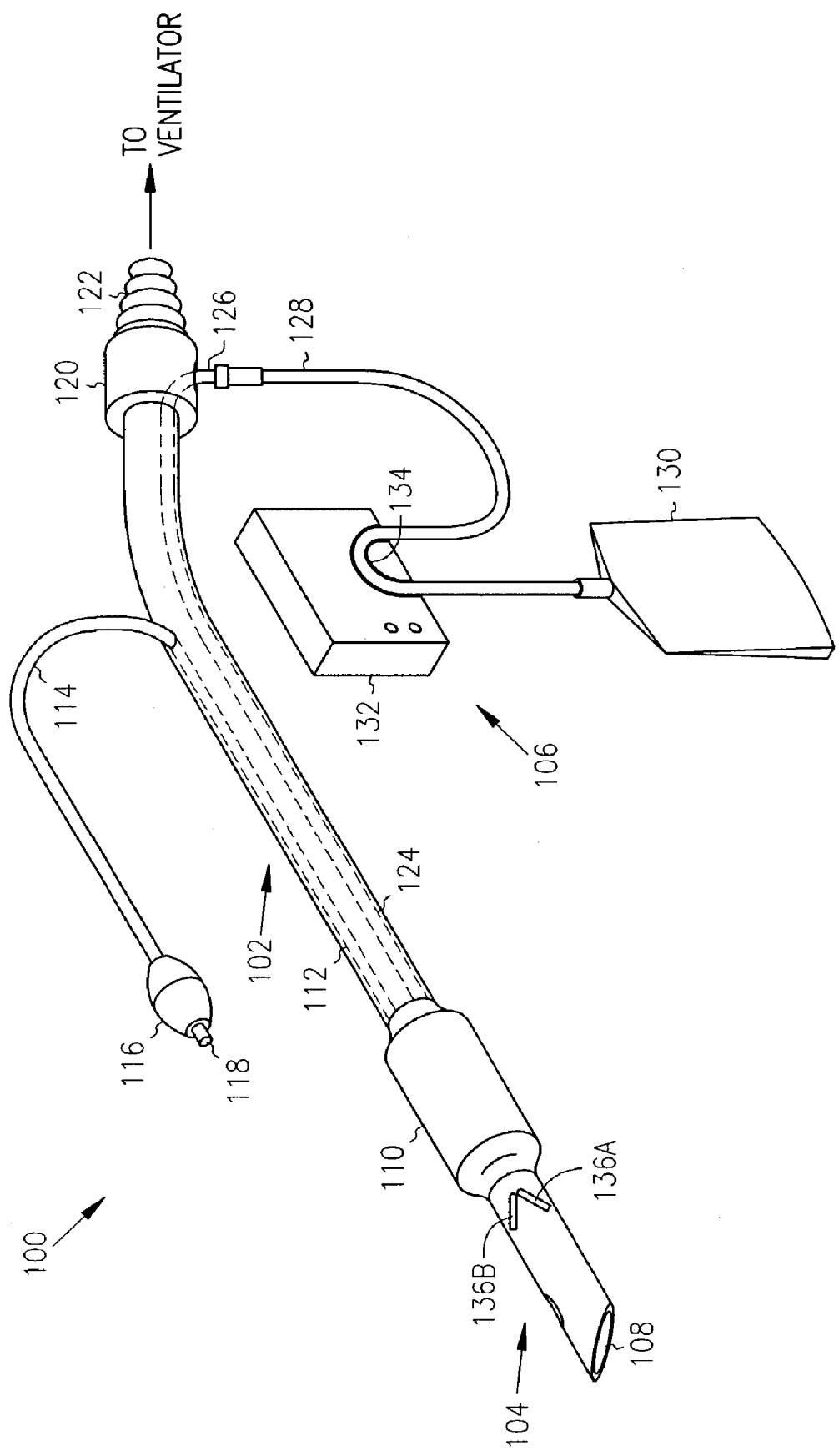
FIG. 1 is a perspective view of one example of a system including a tracheal tube assembly, a fluid pickup assembly, and a pump assembly.

FIG. 1 is a perspective view illustrating generally, by way of example, but not by way of limitation, one embodiment of a system 100 that includes one example of a tracheal tube assembly 102, a fluid pickup assembly 104 located at or near a distal end of tracheal tube assembly 102, and a pump assembly 106 coupled to a location that is at or near a proximal end of tracheal tube assembly 102. In the example of FIG. 1, tracheal tube assembly 102 includes an air passage 108, extending longitudinally between the distal and proximal ends of tracheal tube assembly 102. A bladder-like inflatable cuff 110 (or other seal) is located about the outer circumference of tracheal tube assembly 102 near its distal end. Inflatable cuff 110 is located above (more proximal than) fluid pickup assembly 104. A cuff lumen 112 extends through tracheal tube assembly 102 from cuff 110 to the proximal end portion of tracheal tube assembly 102. For example, cuff lumen 112 may run integrally within a wall of tracheal tube assembly 102, or as a separate tube extending through air passage 108.

In this example, at the proximal end portion of tracheal tube assembly 102, cuff lumen 112 is coupled in fluid communication with external cuff tube 114, which extends outwardly therefrom toward cuff pressure bladder 116 and inflation port 118, or similar pump device for inflating cuff 110. Cuff 110 is capable of being inflated when tracheal tube assembly 102 is disposed within a lumen (e.g., within a patient's trachea). Inflating cuff 110 provides a seal that ensures that airflow occurs within air passage 108, rather than through the trachea outside tracheal tube assembly 102. In one example, cuff 110 is inflated by introducing air into inflation port 118, and by then compressing cuff pressure bladder 116 to force the air through external cuff tube 114 and cuff lumen 112 into cuff 110. The proximal end of tracheal tube assembly 102 terminates at an end connector 120. In this example, end connector 120 is sized and shaped to allow coupling to a ventilator tube 122, which, in turn, is coupled to a mechanical lung ventilator. End connector 120 provides fluid communication between ventilator tube 122 and air passage 108 of tracheal tube assembly 102.

In the example of FIG. 1, fluid pickup assembly 104 is located at the distal end of tracheal tube assembly 102. Therefore, in this example, when the distal end of tracheal tube assembly 102 is introduced into a patient's trachea, fluid pickup assembly 104 is located within the patient below (more distal than) inflatable cuff 110. A fluid removal lumen 124 extends and provides fluid communication between fluid pickup assembly 104 (located at or near the distal end of tracheal tube assembly 102) and a coupling stem 126 (located at or near the proximal end of tracheal tube assembly 102) or a like coupling device. A fluid removal tube 128 is coupled in fluid communication with coupling stem 126, for further carrying the fluid being removed to a bag or other holding receptacle 130. In this example, pump assembly 106 includes a constant volume (CV) or other low volume pump 132, having a pump head 134 coupled to a portion of fluid removal tube 128 for providing a negative pressure within fluid removal tube 128. This assists in drawing a liquid column through fluid removal tube 128 to holding receptacle 130.

In this example, fluid pickup assembly 104 includes at least one wicking fluid pickup port 136A–B. That is, the at least one fluid pickup port 136A–B is sized, shaped, made of a particularly selected material, and/or otherwise configured to use interfacial surface energy (also referred to as surface tension) to introduce a bodily or other fluid (such as mucus or the like) into the at least one wicking fluid pickup port 136A–B. Interfacial surface energies cause a resulting "skin" to form (or, conversely, a repulsion to occur) at an air/liquid interface boundary. Similarly, an attraction or repulsion between a liquid fluid and its interface boundary with a solid may result because of its interfacial surface energy. This interfacial edge effect can provide a capillary action whereby a liquid is pulled into a small pipe, i.e., a capillary. The relative value of the surface energy of the solid wall and that of the liquid determines whether the liquid is more attracted to the wall (in which case a "wicking" occurs which pulls the fluid to the wall) or to itself (in which case it avoids "wetting" the wall). In the present case, the relative value of the surface energy will be affected by, among other things, the size of the at least one fluid pickup port 136A–B, the shape of the at least one fluid pickup port 136A–B, and the material characteristics of the portion of fluid pickup assembly 104 in which the at least one fluid pickup port 136A–B is formed, and the characteristics of the air/fluid interface.

In the example of FIG. 1, fluid pickup assembly 104 is designed to use the interfacial surface energy to draw the mucus or the like into the at least one fluid pickup port 136A–B of pickup assembly 104. Such fluid introduction by wicking advantageously avoids potential damage to the windpipe sidewalls that might occur upon inserting a conventional airflow-based suctioning device through air passage 108 after disconnecting tracheal tube assembly 102 from the ventilator. In the example of FIG. 1, once the mucus or the like pulls itself into the at least one fluid pickup port 136A–B of fluid pickup assembly 104 using the surface energy effect, it is then subjected to a negative pressure, such as that generated by remote external constant volume pump 132, to draw such fluid toward holding receptacle 130.

In this example, fluid removal lumen 124, coupling 126, and fluid removal tube 128 are each sized, shaped, made of a particularly selected material, or otherwise configured such that the surface energy of the mucus (or similar bodily fluid) causes a "skin" to bridge the entire interior cross section of the conduit formed by these components. As a result, a column of mucus is pulled by pump 132 through the conduit provided by these components (recognizing that some suspended gas bubbles or solids may be present in the mucus column being pulled by pump 132). By contrast, conventional airflow-based vacuum devices generally pull liquid fluid by using a large ratio of entrapping air (or other gaseous substance) to the liquid fluid being entrapped by the air. This is because such airflow-based vacuum devices typically depend on the air movement at the intake port to draw the fluid into the port, rather than using surface energy to draw fluid (i.e., "wick" the fluid) into the intake port.

Although not required, in one example, the pressure provided by pump 132 is adjusted to remove fluid at a desired steady-state rate that is selected such that the extracted material passing through the conduit provided by fluid removal lumen 124, coupling 126, and fluid removal tube 128 is almost all liquid (including, among other things, viscous liquids and liquid suspensions bearing suspended solids and/or entrapped gas bubbles), rather than a liquid in combination with a more than insubstantial amount of air or other gaseous substance. This results from the wicking of the mucus or like fluid into the at least one fluid pickup port 136A–B using surface energy. Similarly, the degree of wicking provided by the at least one fluid pickup port 136A–B can be adjusted to match or approximate the subject's mucus generation rate.

In one example, at least a portion of the conduit provided by fluid removal lumen 124, coupling 126, and fluid removal tube 128 (at least up to pump head 134) is designed in material and size such that liquid fluid being transported can span a the inside diameter of said conduit. The design is such that any air bubbles introduced at the at least one fluid pickup port 136A–B preserve an intact air/liquid "skin" or "bridge" that spans the inside diameter of said conduit. As a result, such air bubbles can be conceptualized as being carried along by the liquid column being transported as if they were a part of that liquid column. Therefore, entrapment by high airflow is not required or used to obtain the desired mucus removal. The components forming the conduit are sufficiently rigid to prevent their collapse under the pressures used to move the fluid up against gravity and to overcome the viscosity and holding power of any fluid bridging the fluid pickup ports 136A–B.

Because the fluid removal conduit is occluded by mucus or by the low volume pump 132, such fluid removal does not interfere with the ventilation of the patient being provided through air passage 108, as might be the case with a conventional airflow-assisted fluid removal. As one consequence, the present systems and methods of mucus removal may (but need not) be provided concurrent to the ventilation of the patient, such as continuously. This avoids interrupting ventilation of the patient, such as is required to provide airflow-assisted suctioning for fluid removal. Among other things, such continuous mucus removal, therefore, avoids compromising patient breathing, reduces risk of damage and infection to the patient, reduces risk of contamination of the caregiver by waste products, improves the patient quality of life, and/or reduces cost for caregiver and health care provider.

In one example, the inner diameter of at least a portion fluid removal lumen 124 is sized so as to be small enough to permit it to be bridged by the fluid/air "skin" as a result of the interfacial surface tension. The corresponding size of the inner diameter of fluid removal lumen 124 can be conceptually approximated as illustrated below using Equation 1. Equation 1 illustrates that, to obtain the desired bridging, the inner diameter of fluid removal lumen 124 must be small enough such that a column of the liquid of interest (e.g., mucus) can be lifted by surface energy to a height just greater than the height, h, of the meniscus, as illustrated generally by Equation 1.

$$h = \frac{2 \cdot y \cdot \cos\theta_c}{r \cdot P_e \cdot g} \qquad \text{Equation 1}$$

In Equation 1, y is the surface tension value of the fluid, $\theta_c$ is the angle at which the fluid contacts the inner circumference of the fluid removal lumen 124, r is the inner radius of the fluid removal lumen 124, $P_e$ is the fluid density in air, and g is the acceleration due to gravity. Thus, in one example, the size of the inner diameter of fluid removal lumen 124 is increased until h equals the height of the meniscus, as illustrated in Equation 1. Similarly, the size of the inner diameter of the wicking fluid pickup port(s) 136A–B is determined as described with respect to Equation 1.

Figure 2:
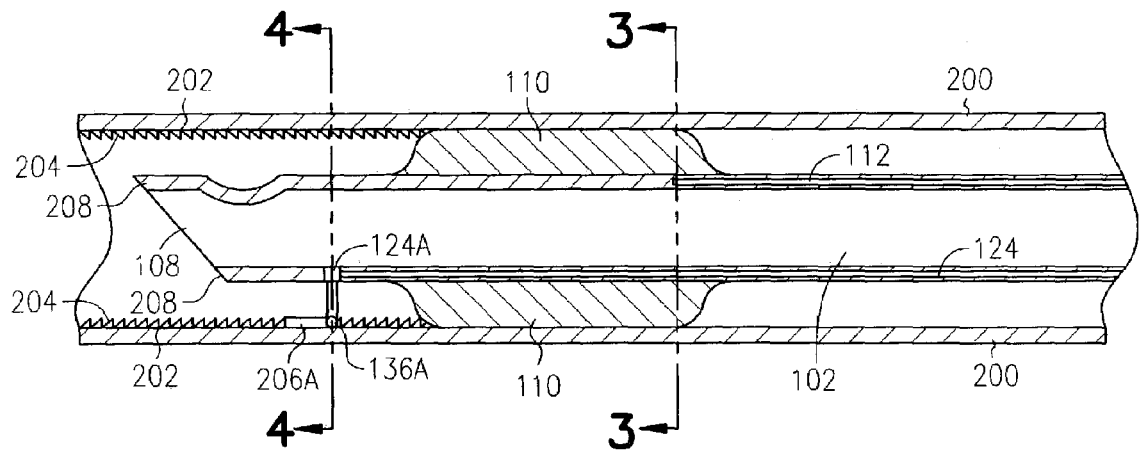
FIG. 2 is a cross-sectional view of one example of a distal portion of the tracheal tube assembly inserted within a portion of a patient's trachea.
Figure 3:
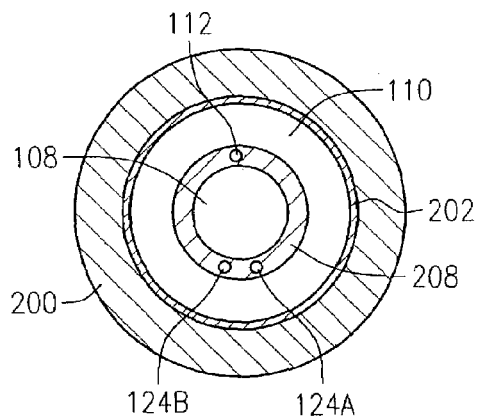
FIG. 3 is a cross-sectional view taken along the cutline 3—3 of FIG. 2.
Figure 4:
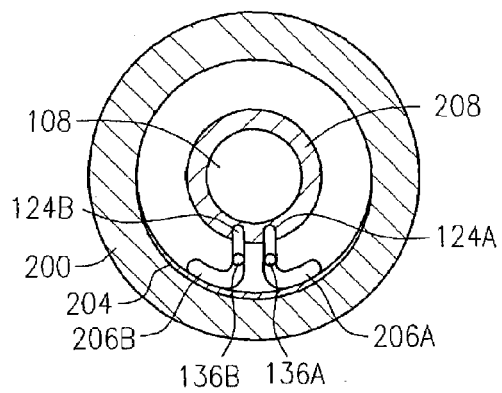
FIG. 4 is a cross-sectional view taken along the cutline 4—4 of FIG. 2.

FIG. 2 is a cross-sectional view illustrating generally, by way of example, but not by way of limitation, one embodiment of a distal portion of tracheal tube assembly 102 inserted within a portion of a patient's trachea 200. FIGS. 3 and 4 are cross-sectional views taken along the respective cutlines 3—3 and 4—4 of FIG. 2. In the example illustrated in FIGS. 2–4, trachea 200 includes an inner tracheal wall 202 upon which a mucus coating 204 has developed. Cuff 110 is illustrated, in this example, as having been inflated to seal trachea 200. In FIG. 2, pickup assembly 104 includes pickup prongs 206A–B extending outwardly from pickup assembly 104, toward mucus coating 204, such as in a bent "V" configuration. Prongs 206A–B assist in collecting the moving sheet of mucus 204, and directing it toward the apex of the bent "V," near which fluid pickup ports 136A–B are located. In this example, each of the fluid ports 136A–B is connected to a separate one of fluid removal lumens 124A–B, which, in this example, extend longitudinally within wall 208 of tracheal tube assembly 102 toward its proximal end. However, in another example, one or more fluid removal lumens 124A–B extends as a tube running longitudinally through air passage 108. In yet another example, one or more fluid removal lumens 124A–B extends as a tube running along an exterior portion of tracheal tube assembly 102, such as by passing beneath cuff 110, or even through cuff 110 (e.g., using appropriately sized folds in the wall of cuff 110 to provide passage through cuff 110). A different number of fluid removal lumens 124 may be provided, for example, corresponding to a different number of fluid pickup ports 136. In one such example, system 100 includes a single fluid pickup port 136 and a corresponding single fluid removal lumen 124.

In one example, portions of system 100 are supplied as a kit including different fluid pickup assemblies 104 (e.g., having differently sized prongs 206A–B). This allows the user to select an appropriately sized pickup assembly 104 to more closely match one of several different possible sizes of trachea 200, which may vary from patient to patient. Also, although FIGS. 1–3 illustrate a pair of fluid pickup ports 136A–B, in another example, a larger number of fluid pickup ports 136 are used. This increases the number of surface energy assisted mucus collection sites. Such fluid pickup ports may be located in many different possible configurations.

Figure 5:
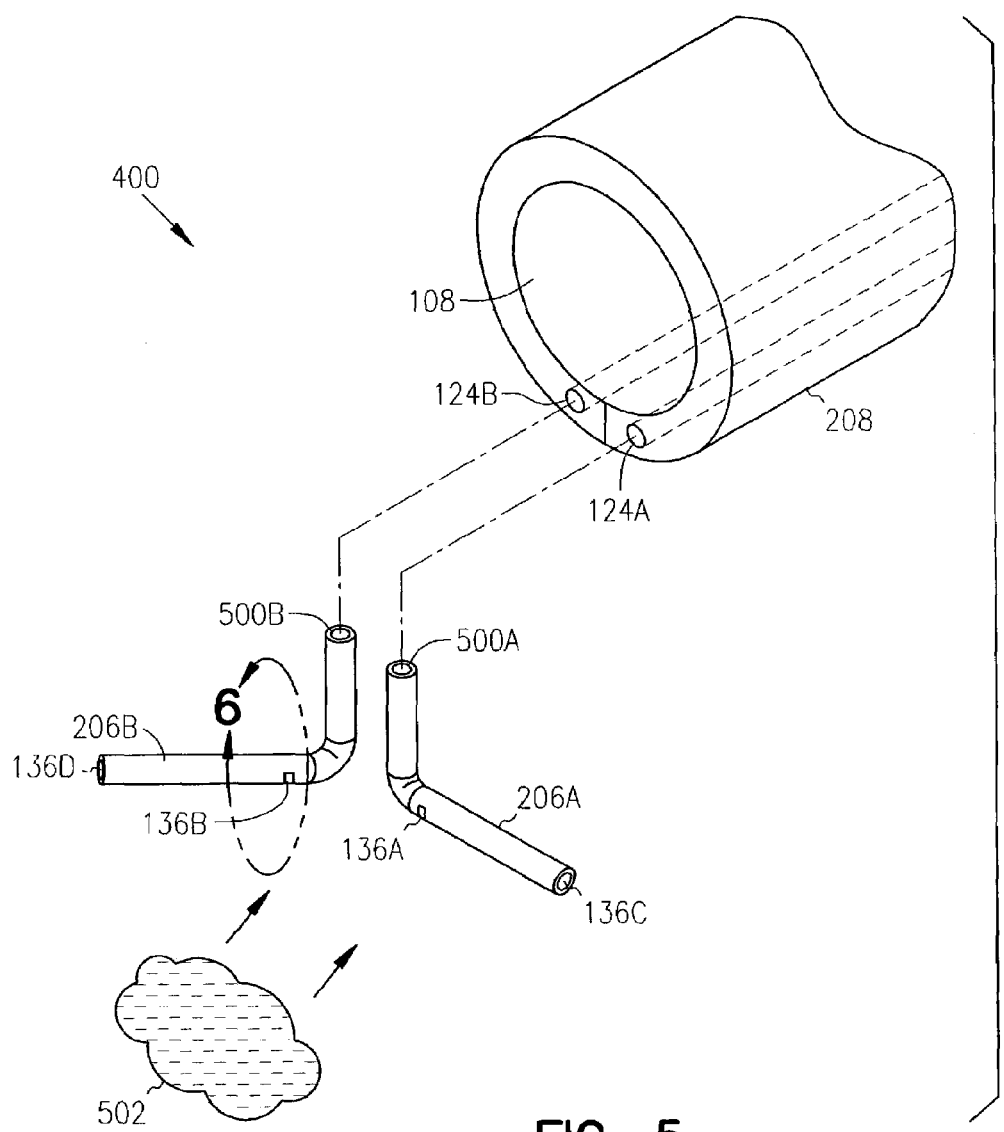
FIG. 5 is an exploded perspective view of one example of a portion of the fluid pickup assembly including hollow tubular bent "V" collection prongs attachable in fluid communication with corresponding fluid removal lumens.
Figure 6:
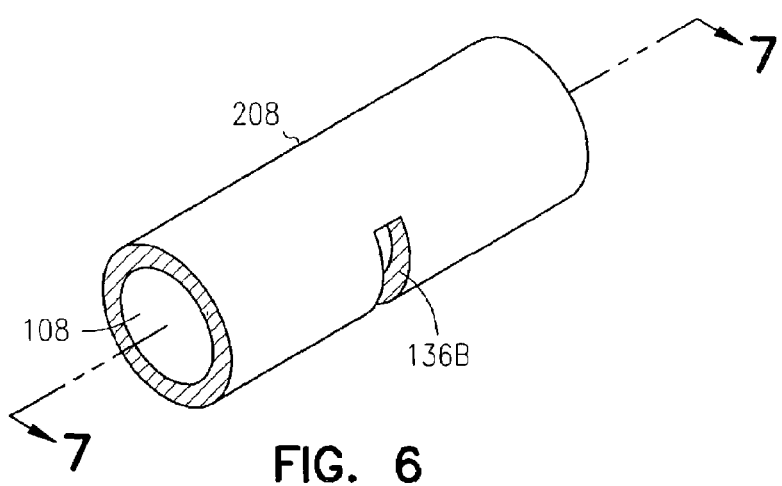
FIG. 6 is a perspective view illustrating in more detail the region 6 in FIG. 5.
Figure 7:
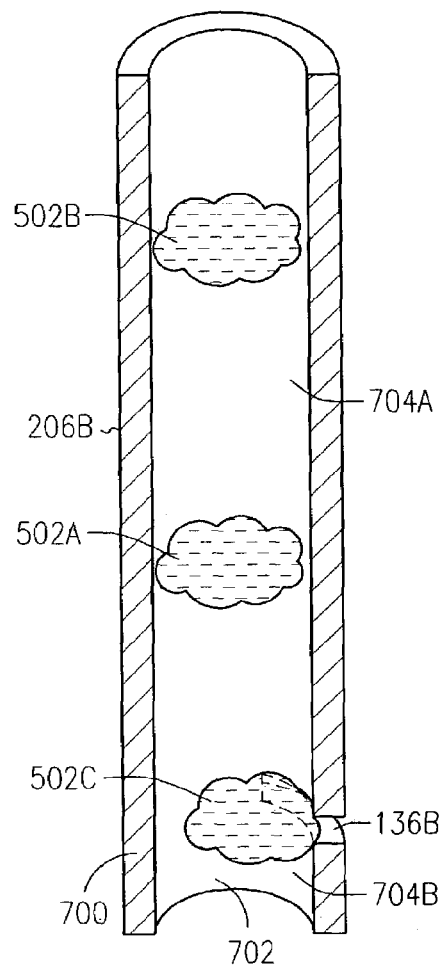
FIG. 7 is a cross-sectional view taken along the cutline 7—7 of FIG. 6.

FIG. 5 is an exploded perspective view illustrating generally, by way of example, but not by way of limitation, one embodiment of a portion of fluid pickup assembly 104 including hollow tubular bent "V" collection prongs 206A–B attachable in fluid communication with corresponding fluid removal lumens 124A–B. In one example, prongs 206A–B are attachable to corresponding fluid removal lumens 124A–B using snap-fit or other coupling ends 500A–B. In this example, 30 fluid pickup ports 136A–B are located near the apex formed by bent "V" collection prongs 206A–B. Additional fluid pickup ports 136C–D are provided, in this example, by the hollow ends of collection prongs 206A–B, which are located opposite from respective coupling ends 500A–B. FIG. 6 is a perspective view illustrating in more detail the region 6 in FIG. 5 near fluid pickup port 136B. FIG. 7 is a cross-sectional view taken along the cutline 7—7 of FIG. 6. FIG. 7 illustrates a wall 700 and lumen 702 of a portion of hollow collection prong 206B.

In one example of operation, such as illustrated in FIGS. 5–7, a liquid mucus plug 502 is collected by prongs 206A–B and directed toward fluid pickup ports 136A–B, which wick mucus plug 502 into hollow prongs 206A–B using surface energy. As illustrated in FIG. 7, mucus plugs 502A–C need not form a completely contiguous liquid passing through lumen 702, but may instead constitute liquid plugs separated by bubbles 704A–B of air or other gasses that travel along with the mucus plugs 502A–C spanning lumen 702; the bubbles typically do not break the bridging or spanning of the mucus plugs across the interior of lumen 702. Because the fluid pickup ports 136A–B are designed with a size, shape, and/or material properties that wick in mucus using surface energy assistance, liquid mucus plugs (e.g., mucus plug 502C in FIG. 7) will bridge and pass unimpeded under fluid pickup port 136B within lumen 702.

In one example, one or more of fluid pickup ports 136A–C is designed to allow it to act as a safety vent for another of fluid pickup ports 136A–C. In one example, fluid pickup port 136A is located on collection prong 206A in such a manner as to likely come into contact with trachea wall 202 for wicking in mucus 204. However, it is possible that the tissue of trachea wall 202 may enter fluid pickup port 136A or may otherwise occlude a significant portion of fluid pickup port 136A. In this example, fluid pickup port 136C is located on collection prong 206A in such a manner so as to likely avoid contact with trachea wall 202 when fluid pickup port 136A contacts trachea wall 202 (e.g., by orienting fluid pickup ports 136A and 136C in different directions, such as illustrated in FIG. 5). Because fluid pickup ports 136A and 136C do not likely concurrently contact trachea wall 202, if one of these fluid pickup ports 136A and 136C becomes occluded by such contact, the other of these fluid pickup ports 136A and 136C limits the pressure buildup within the conduit formed by lumen 702 of hollow collection prong 206A, fluid removal lumen 124A, coupling 126, and distal portion of fluid removal tube 128. The pressure buildup is limited to the pressure needed to break the surface tension of the mucus entering such other these fluid pickup ports 136A and 136C, which is acting as a safety vent. Using such a safety vent arrangement to limit pressure buildup reduces or avoids the risk of damage to any portion of trachea wall 202 that enters within or otherwise occludes one of the fluid pickup ports 136A and 136C. The "safety pressure" value to which the pressure buildup is limited is determined by the size and surface energy determining material characteristics of fluid pickup port 136C. In an alternative example, a separate safety vent port is provided, rather than using one of the fluid pickup ports 136A–D as a safety vent port. This may be advantageous in tailoring the safety pressure value of the safety vent port.

Figure 8:
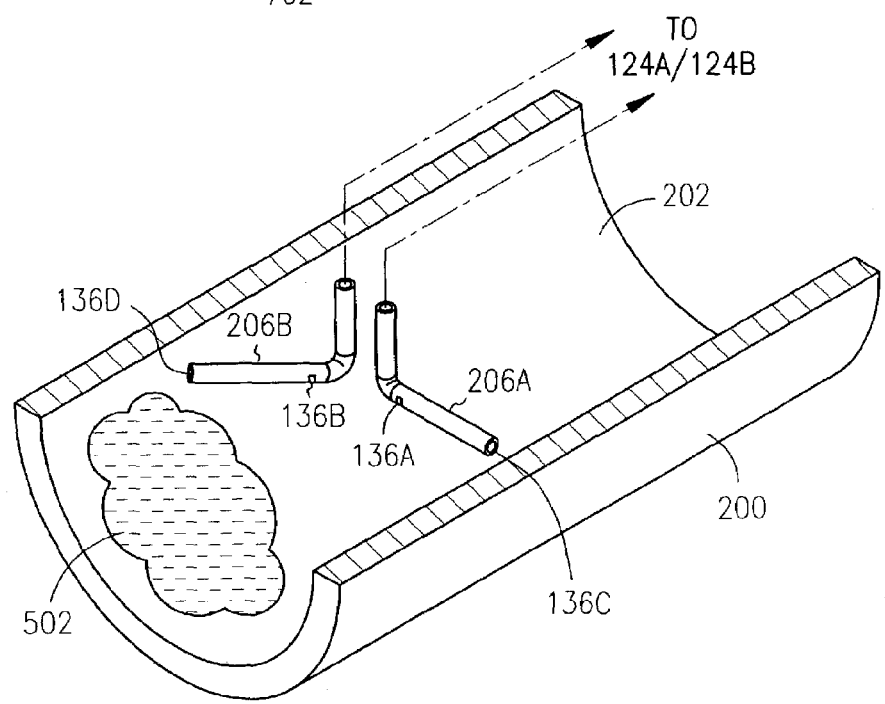
FIG. 8 is an exploded perspective view of one example of a portion of the pickup assembly, illustrating collection prongs located within a trachea.

FIG. 8 is an exploded perspective view illustrating conceptually, by way of example, but not by way of limitation, one embodiment of a portion of pickup assembly 104, that is, collection prongs 206A–B within trachea 200, such as for collecting mucus 502 and directing it towards fluid pickup ports 136A–B near the apex of the bent "V" collection prongs 206A–B.

Figure 9A:
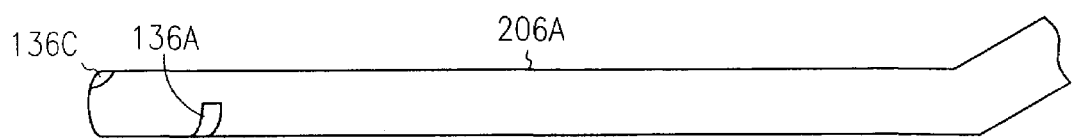
FIGS. 9A, 9B, 9C, 9D, 9E, and 9F are conceptualized schematic diagrams of one example of operation of portions of a fluid pickup assembly including a collection prong and fluid pickup ports.
Figure 9B:
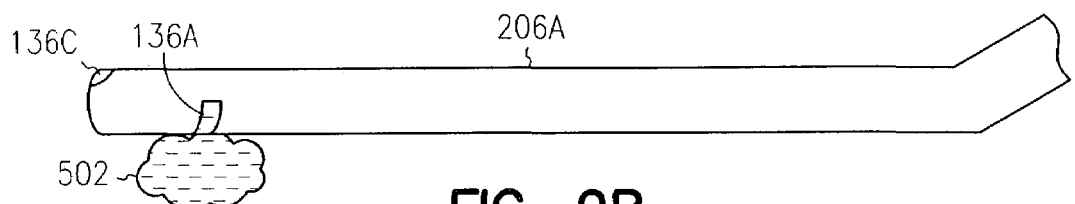
Figure 9C:
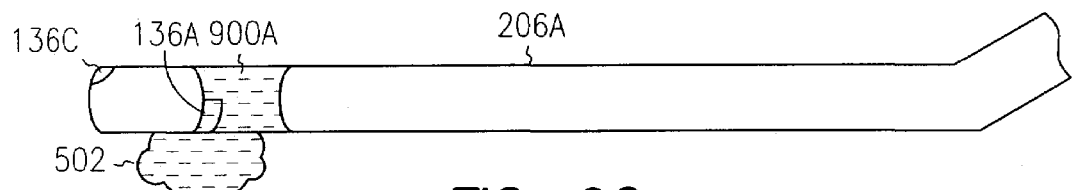
Figure 9D:
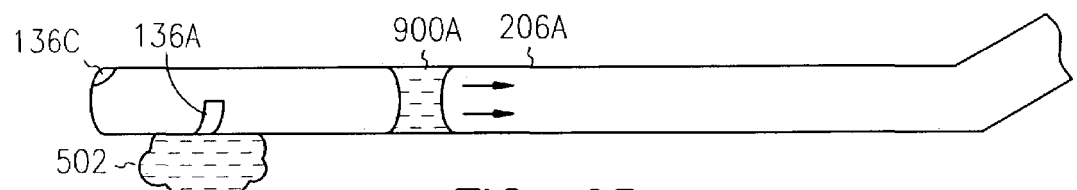
Figure 9E:
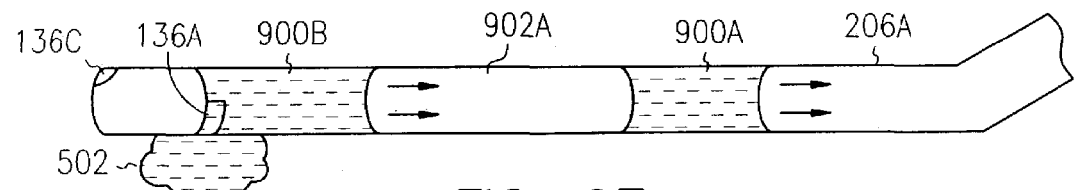
Figure 9F:
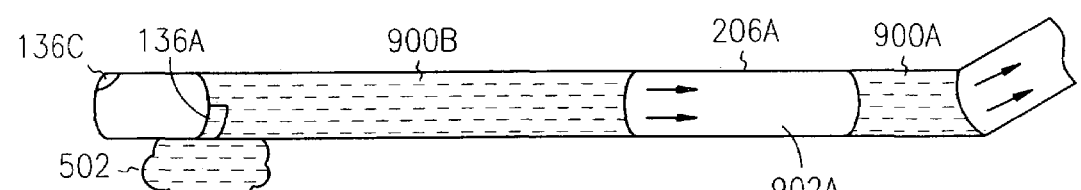

FIGS. 9A–9F are conceptualized schematic diagrams illustrating generally, by way of example, but not by way of limitation, operation of portions of a fluid pickup assembly 104 including a collection prong 206A and fluid pickup ports 136A and 136C. FIG. 9A illustrates liquid mucus 502 outside of collection prong 206A and not touching fluid pickup port 136A. FIG. 9B illustrates mucus 502 wicking into fluid pickup port 136A. FIG. 9C illustrates a resulting wicked-in liquid mucus plug 900A forming within the hollow lumen of collection prong 206A. Wicked-in mucus plug 900A is urged toward the conduit to holding receptacle 130 by pump 132. FIG. 9D illustrates mucus plug 900A moving toward holding receptacle 130. FIG. 9E illustrates a second mucus plug 900B wicking into fluid pickup port 136A, separated from mucus plug 900A by an air bubble 902A that moves together with mucus plugs 900A–B. FIG. 9F illustrates further formation of a large wicked-in mucus plug 900B.

Figure 10:
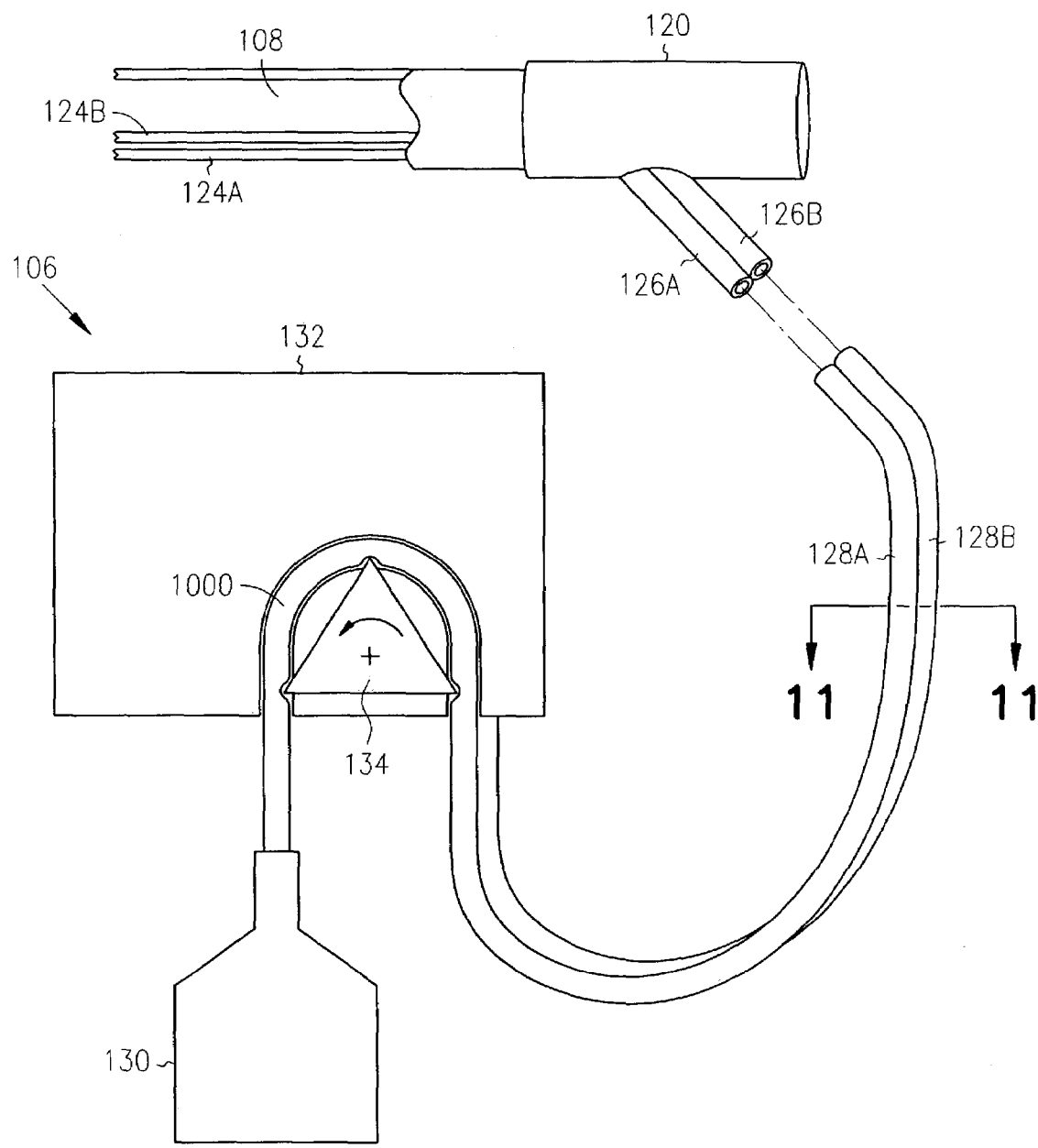
FIG. 10 is an exploded perspective view of one example of portions of a pump assembly, which is couplable to portions of the tracheal tube assembly.
Figure 11:
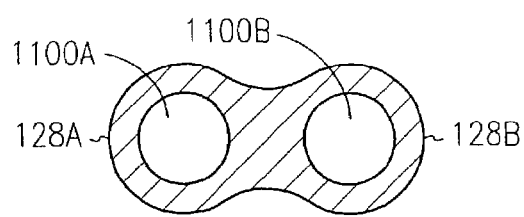
FIG. 11 is a cross sectional view of a portion of the pair of fluid removal tubes taken along the cutline 11—11 of FIG. 10.

FIG. 10 is an exploded perspective view illustrating generally, by way of example, but not by way of limitation, one embodiment of portions of pump assembly 106, which is configured for coupling to a portion of tracheal tube assembly 102. This example illustrates dual fluid removal lumens 124A–B in separate fluid communication with respective dual couplings 126A–B, which, in turn, are configured for separate fluid communication with respective dual fluid removal tubes 128A–B. FIG. 11 is a cross sectional view of a portion of the pair of fluid removal tubes 128A–B taken along the cutline 11—11 of FIG. 10. FIG. 11 illustrates an example in which dual fluid removal tubes 128A–B are joined in a single tube assembly that provides separate lumens 1000A–B. In the example of FIG. 10, a portion of fluid removal tubes 128A–B near pump head 134 is flexible (other portions may also be flexible). In one embodiment, pump 132 is a peristalsis pump, with a triangular solid rotating pump head 134 that wipes against and compresses a flexible portion of fluid removal tubes 128A–B. This rotational "kneading" urges the liquid fluid 1000 toward holding receptacle 130. This, in turn, creates a negative pressure within more distal portions of lumens 1100A–B, which, in turn, urges additional fluid toward pump 132.

Thus, in this example, pump 132 provides a negative pressure such that entrapment of fluid 1000 by airflow is not required to transport the fluid toward holding receptacle 130. A peristalsis pump is only one example of a constant volume (CV) pump capable of supplying a negative pressure against the fluid 1000. Alternative embodiments may use one or more other types of low volume pumps, which need not be CV pumps, and which may be operated intermittently. Some other pump examples include, among other things, an accordion-style cavity with one-way valves for intake and discharge, such that repeated compressing of the cavity transports the fluid.

Operation of the example illustrated in FIGS. 1–11 uses fluid pickup ports 136 sized and shaped and having material properties that "wick" the mucus into the fluid transport conduit that includes fluid removal lumens 124, coupling 126, and fluid removal tubes 128. After the mucus has been introduced into the conduit, it is urged toward holding receptacle 130, such as by using negative pressure that does not require entrapment of the transported mucus by passing airflow. Portions of the conduit may be integrally formed with tracheal tube assembly 102 (e.g., as longitudinal lumens therethrough) otherwise affixed to tracheal tube assembly 102 (e.g., as one or more tubes affixed using glue or other mechanical affixation techniques), or even as at least one catheter or other tube introduced through air passage 108 of tracheal tube assembly 102 without relying on affixation to tracheal tube assembly 102.

Figure 12:
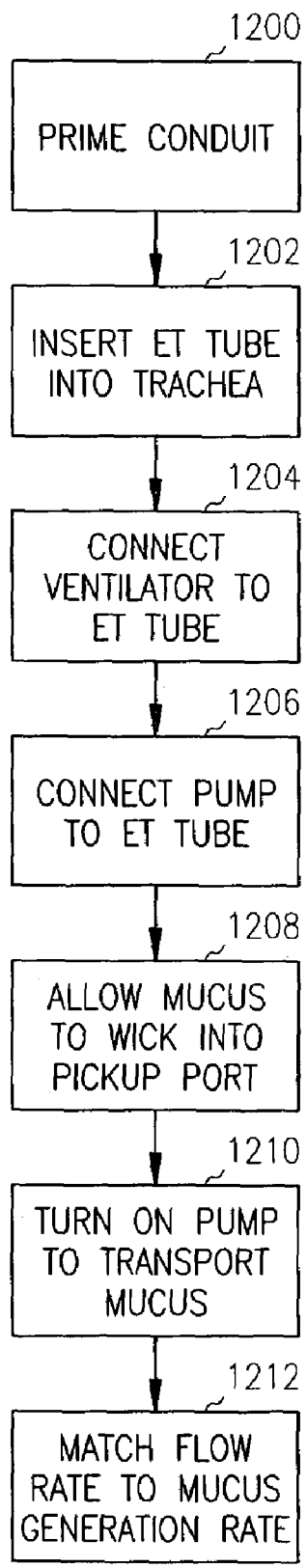
FIG. 12 is a flow chart of one example of operation of portions of the system for removing mucus during mechanical ventilation of a patient using the tracheal tube assembly.

FIG. 12 is a flow chart illustrating generally, by way of example, but not by way of limitation, one embodiment of operating portions of system 100 for removing mucus during mechanical ventilation of a patient using a tracheal tube assembly 100. Although not required, in the example of FIG. 12, at 1200, the fluid transport conduit (or, alternatively, only a distal end portion thereof) is primed with a sterile water solution that has surface tension characteristics similar to the lung mucus of the patient. In one example, this matching of the surface tension characteristic of the priming solution to that of the lung mucus results in avoiding leakage of the priming solution from the conduit (e.g., out of a fluid pickup port 136). At 1202, tracheal tube assembly 102 is then inserted into trachea 200. At 1204, end connector 120 of tracheal tube assembly 102 is coupled to the mechanical ventilator. At 1206, pump assembly 106 and holding receptacle 130 are connected to tracheal tube assembly 102, such as by connecting at least one fluid removal tube 128 to coupling 126. In one example, holding receptacle 130 includes a waste bag. The waste bag is initially collapsed. The waste bag will expand with the collected mucus and any accumulated air bubbles that are discharged by pump 132.

At 1208, once the tracheal tube assembly 102 is in place for a short period of time, the mucus 204 on the inner wall 202 of trachea 200 will wick onto and then into the at least one fluid pickup port 136A–B. At 1210, pump 132 is turned on. This creates a negative pressure in the conduit. As a result, the priming solution—and then the wicked-in mucus—is transported through the conduit toward holding receptacle 130. In one example, at 1212, the flow rate of the mucus is selected such that it approximately matches the mucus generation rate of the lungs. This avoids mucus accumulating below cuff 110 by using too low of a flow rate. This also avoids filling holding receptacle 130 with possibly contaminated air by using too high of a flow rate. This also preserves the bridging skin of the liquid mucus across the at least one fluid pickup port 135A–B, or across a safety vent or the like, such as discussed elsewhere in this document.

In one operational variation, the direction of fluid transport through the conduit is reversed, such as for introducing medicine and/or irrigation fluid or the like through the conduit and out of the at least one fluid pickup port 136A–B. For example, delivery of irrigation fluid to the pickup area within trachea 200 may aid in softening hardened mucus, or even in dissolving mucus castings. Therefore, system 100 is adapted to accommodate mucus of different consistencies.

In one example, the medicine, irrigation fluid, or the like is introduced by swapping in a different holding receptacle 130 (carrying the drug, irrigation fluid, or the like) and reversing the direction of pump 132. In another example, a different holding receptacle and/or pump is used for fluid delivery to the patient.

In one example, the medicine and/or irrigation fluid or the like has a different surface energy characteristic from the mucus for which the fluid transport conduit and pickup ports 136A–B were designed. Under certain such circumstances, therefore, the medicine and/or irrigation fluid or the like is not retained within the conduit by the wicking (in contrast to the priming solution discussed above). Therefore, such medicine and/or irrigation fluid may be delivered out of the same pickup ports 136A–B that wick-in mucus.

In another variation, in which the patient's lungs are irrigated by a medicinal or other irrigation fluid (either using system 100, or otherwise), system 100 is used to remove excess irrigation fluid using one or more fluid pickup ports 136A–B that is particularly designed to wick in the irrigation fluid. In one such example, the irrigation fluid is introduced and removed through different ports, which are tailored to provide these different functions.

In another example, the surface energy characteristics of the at least one pickup port 136A–B and/or the conduit are changed during the introduction of the medicine and/or irrigation fluid or the like. In one example, a temporary modulation of the surface energy at a particular location (e.g., within at least one pickup port 136A–B or within one or more portions of the fluid transport conduit) may be obtained by introducing a surfactant. In another example, at least one electrode (e.g., at or near the at least one pickup port 136A–B) modulates a local surface energy characteristic and/or provides an electric field that assists in expelling a drug or other fluid out of the at least one pickup port 136A–B. In a further example, an electric field is applied to the electrode to adjust the rate at which the drug is introduced into the patient. In one example, the electrode is located at or near the at least one pickup port 136A–B, and is connected to a wire that extends longitudinally through tracheal tube assembly 102, from at or near its distal end to at or near its proximal end, for coupling the electrode to an external electrical energy source.

Modifying the surface energy characteristic at the at least one pickup port 136A–B and/or within the fluid transport conduit is not restricted to the above example of introducing a drug, fluid, or the like into a patient. In one example, the surface energy characteristics varies at one or more different locations of the at least one pickup port 136A–B and along the fluid transport conduit. Such variations are obtained, in one example, by varying the size, shape, and/or material characteristics at these one or more different locations. Moreover, a needed change in lumen size at a particular location in the at least one pickup port 136A–B or the fluid transport conduit may be offset, if needed, by a corresponding change in another surface tension affecting characteristic (e.g., material property, embedded electrode, etc.) at that location to preserve the bridging or sealing action, at that location, of the fluid being transported. In another example, a change in a surface tension affecting characteristic is used to preserve a spanning fluid/air interface bridge or to otherwise accommodate a branching or other junction of fluid transportation lumens, such as wherein an increased diameter is desired.

Figure 13:
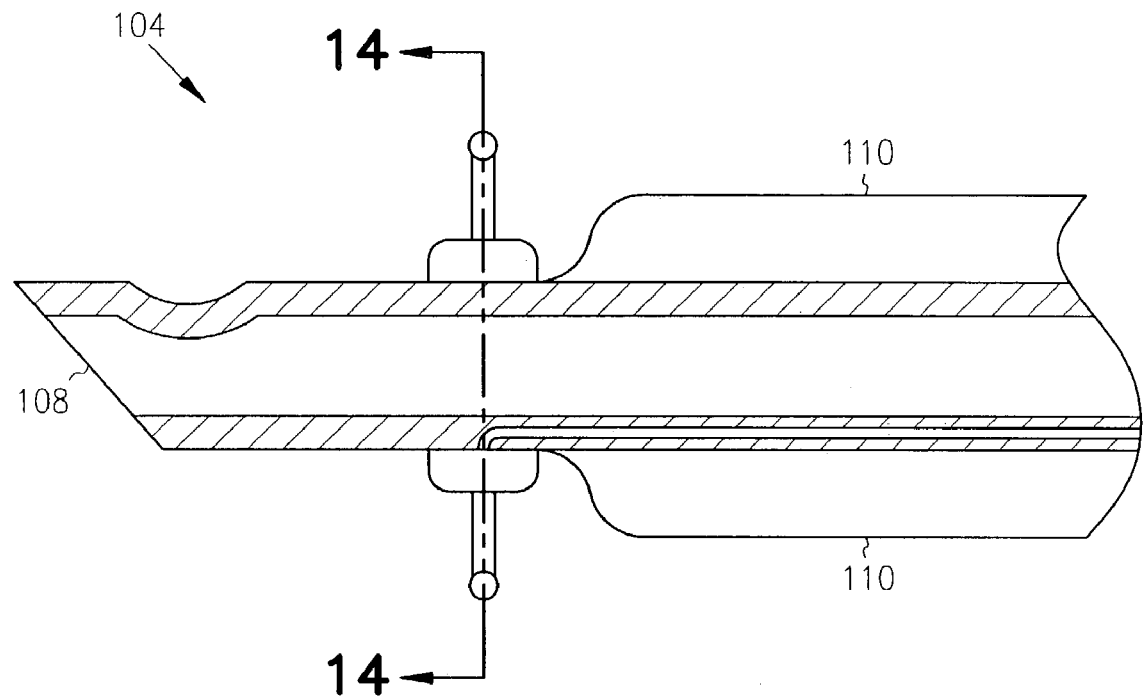
FIG. 13 is a cross-sectional side view of one example of a portion of a fluid pickup assembly that includes a pair of fluid collection prongs located on an opposite side of the fluid pickup assembly from another pair of fluid collection prongs.
Figure 14:
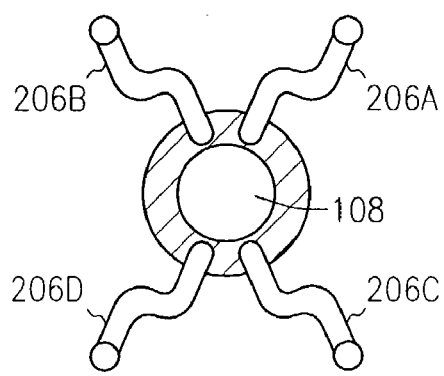
FIG. 14 is a cross-sectional view taken along the cutline 14—14 of FIG. 13.

FIG. 13 is a cross-sectional side view illustrating generally, by way of example, but not by way of limitation, one embodiment of a portion of a fluid pickup assembly 104 that includes fluid collection prongs 206A–B located on an opposite side of fluid pickup assembly 104 from fluid collection prongs 206C–D. This allows contact with multiple different regions of the inner wall 202 of trachea 200. FIG. 14 is a cross-sectional view taken along the cutline 14—14 of FIG. 13. More generally, in another embodiment, other or additional collection prongs 206 (or other devices carrying fluid pickup ports) are radially or otherwise distributed about the circumference of fluid pickup assembly 104 for providing additional fluid collection sites. In one example, each collection prong 206 provides at least one fluid pickup port 136 that is in fluid communication with a separate fluid removal lumen 124. However, in another example, one or more such fluid removal lumens 124 are shared between different fluid pickup ports 136. The fluid removal lumens 124 may be integrally formed within the wall of tracheal tube assembly 102 or, alternatively, may be separately formed and attached within air passage 108, or on the outside wall, of tracheal tube assembly 102. In one example, collection prongs 206 are flexible so as to conform to the size of trachea 200, that is, to touch or come in close proximity with wall 202 of trachea 200.

Figure 15:
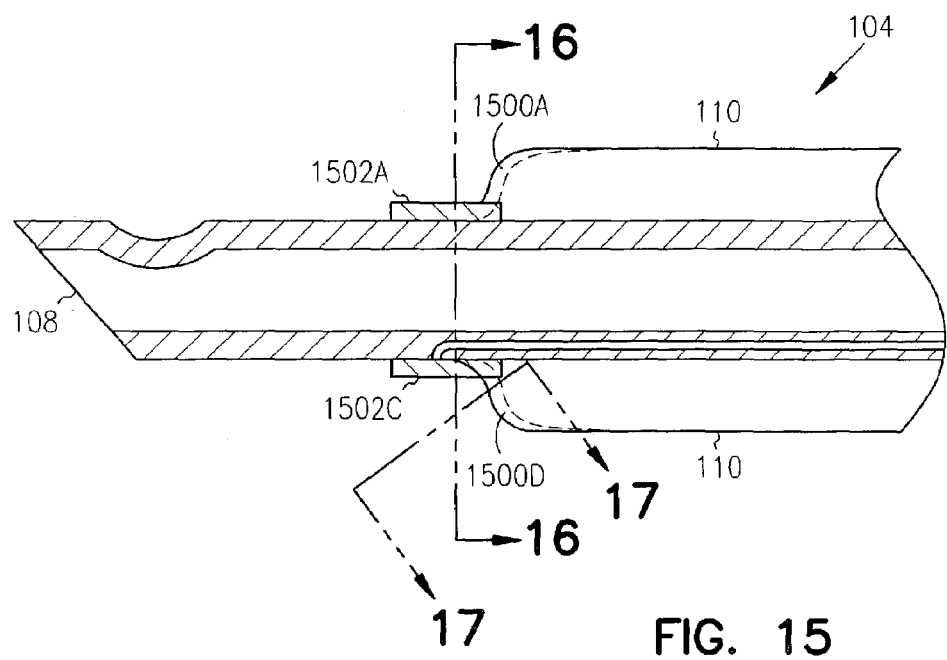
FIG. 15 is a cross-sectional side view of one example of a portion of a fluid pickup assembly using a distal sidewall portion of a cuff for wicking mucus toward entry portals.
Figure 16:
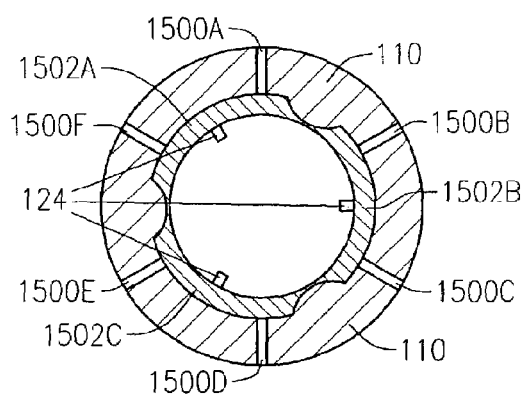
FIG. 16 is a cross-sectional view taken along the cutline 16—16 of FIG. 15.
Figure 17:
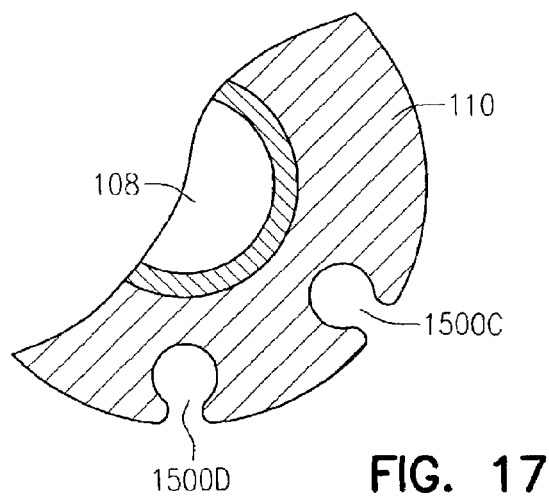
FIG. 17 is a cross-sectional view taken along the cutline 17—17 of FIG. 15.

FIG. 15 is a cross-sectional side view illustrating generally, by way of example, but not by way of limitation, one embodiment of a portion of a fluid pickup assembly 104 using a distal sidewall portion of cuff 110 for wicking mucus toward entry portals. FIG. 16 is a cross-sectional view taken along the cutline 16—16 of FIG. 15. FIG. 17 is a cross-sectional view taken along the cutline 17—17 of FIG. 15. In the example of FIGS. 15–17, mucus moving upward from the patient's lungs, along wall 202 of trachea 200, will tend to collect at the obstructing distal sidewall portion of cuff 110. In this example, the distal sidewall portion of cuff 110 includes wicking troughs, tubes, grooves, or channels 1502A–F, such as extending radially outward from at least one wicking fluid collection manifold 1502A–C. In one example, channels 1500 are constructed of a nearly complete fold in the material of cuff 110 such that only a small slit is left open. The slit is sized such that the mucus wicks into the channel 1500 while still bridging the slit.

In this example, each fluid collection manifold 1502A–C is coupled in fluid communication with at least one fluid removal lumen 124 (such as illustrated in FIG. 16) extending toward the proximal end of tracheal tube assembly 102. In this example, mucus collects in the wicking channels 1500 formed in the distal sidewall portion of cuff 110. The mucus is wicked through channels 1500 toward and into respective collection manifolds 1502. The mucus is then transported toward and into corresponding fluid removal lumens 124, either by wicking or by the aid of the pump 132, or both. Upon entering fluid removal lumens 124, the mucus is urged toward the proximal end of tracheal tube assembly 102 by pump 132.

Figure 18:
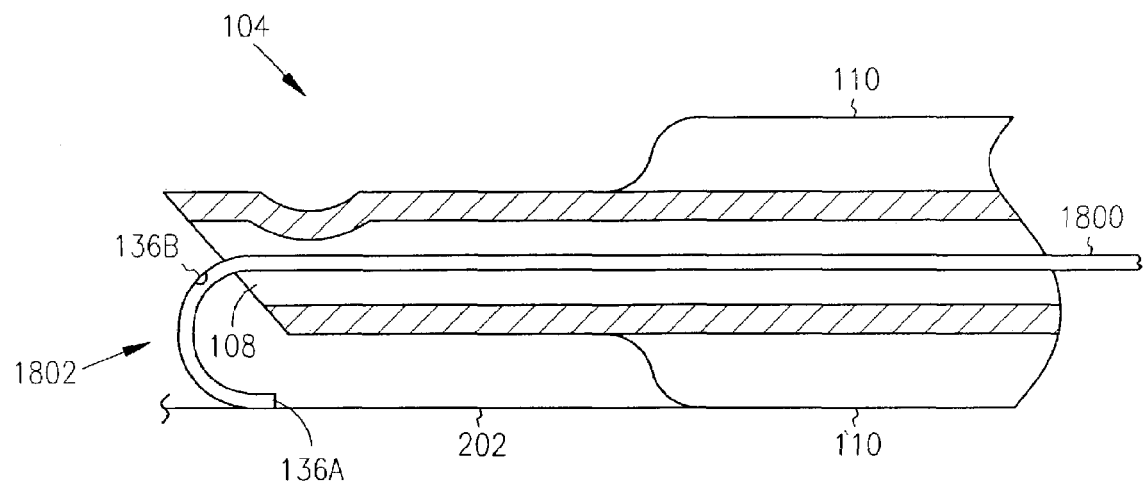
FIG. 18 is a cross-sectional side view of one example of fluid pickup assembly portions of the system.

FIG. 18 is a cross-sectional side view illustrating generally, by way of example, but not by way of limitation, one embodiment of fluid pickup assembly 104 portions of system 100. In this example, system 100 includes a fluid removal tube 1800 that is sized and shaped such that it can be fed through air passage 108 without substantially interfering with patient ventilation through air passage 108. In the illustrated example, fluid removal tube 1800 includes a shape-memory characteristic such that its distal end 1802 forms a J-shape upon exiting the distal end of air passage 108. This allows distal end 1802 of fluid removal tube 1800 to bend outward toward, and to come in contact with, tracheal wall 202. By slightly retracting a proximal end of fluid removal tube 1800, the J-shaped distal end 1802 may be seated against tracheal wall 202. At least one wicking fluid pickup port 136A is located such that it contacts tracheal wall 202 for wicking in mucus. In one example, at least one fluid pickup port 136B provides a safety vent, as discussed above, by being positioned on the J-shaped distal end 1802 such that it likely does not contact tracheal wall 202 concurrent to such contact by fluid pickup port 136A. Although FIG. 18 illustrates a J-shaped distal end 1802 for contacting wall 202 of trachea 200, other shapes of distal end 1802 will obtain similar contact (e.g., an O-shape, a spiral-shape, or the like). Such shape variants provide additional or differently distributed fluid collection sites within trachea 200. In one example, fluid removal tube 1800 is long enough such that, when inserted through air passage 108, distal end 1802 is located at or near that portion of trachea 200 that branches into separate bronchial tubes, or even located within one of the patient's bronchial tubes. This, in turn, positions the at least one wicking fluid entry portal 136A–B deep in trachea 200, or in one of the patient's bronchial tubes, for removing fluid therefrom to further enhance fluid removal from the patient.

Figure 19:
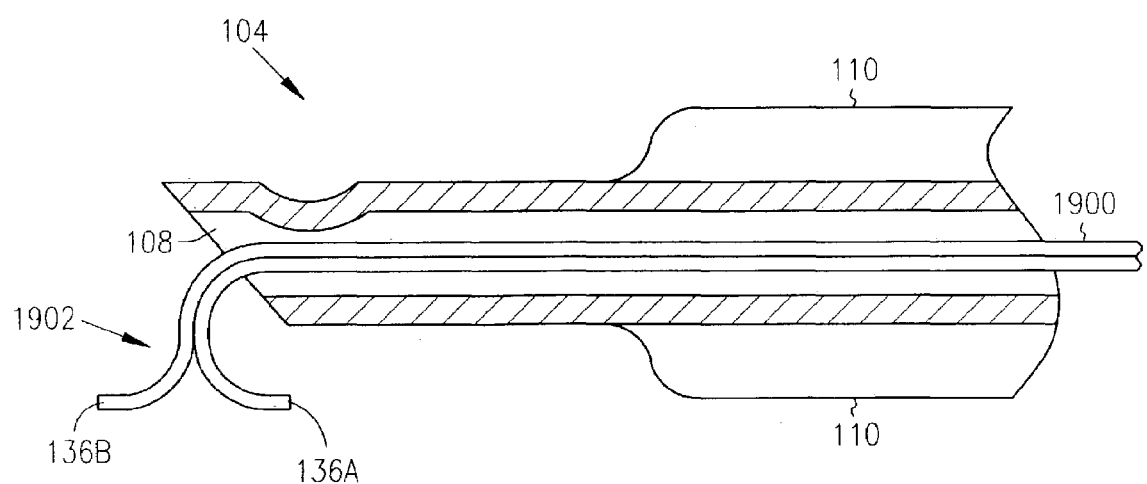
FIG. 19 is a cross-sectional side view of one example of fluid pickup assembly portions of the system.

FIG. 19 is a cross-sectional side view illustrating generally, by way of example, but not by way of limitation one embodiment of fluid pickup assembly 104 portions of system 100. In this example, system 100 includes a multilumen fluid removal tube 1900 that is sized and shaped such that it can be fed through air passage 108 without substantially interfering with patient ventilation through air passage 108. In the illustrated example, multilumen fluid removal tube 1900 includes a shape-memory characteristic such that individual lumens at its distal end 1902 flare outwardly upon exiting the distal end of air passage 108. This allows the individual tubular lumens at the distal end 1902 of multilumen fluid removal tube 1900 to bend outward toward, and to come in contact with, tracheal wall 202. By slightly retracting a proximal end of multilumen fluid removal tube 1900, the flared out tubes at the distal end 1902 may be seated against tracheal wall 202. Each such flared out tube includes at least one wicking fluid pickup port 136A, which is located such that it contacts tracheal wall 202 for wicking in mucus. In one example, safety vents are provided, as discussed above. In one example, fluid removal tube 1900 is long enough such that, when inserted through air passage 108, distal end 1902 is located at or near that portion of trachea 200 that branches into separate bronchial tubes, or even located within one of the patient's bronchial tubes. This, in turn, positions the at least one wicking fluid entry portal 136A–B deep in trachea 200, or in one of the patient's bronchial tubes, for removing fluid therefrom to further enhance fluid removal from the patient.

Figure 20:
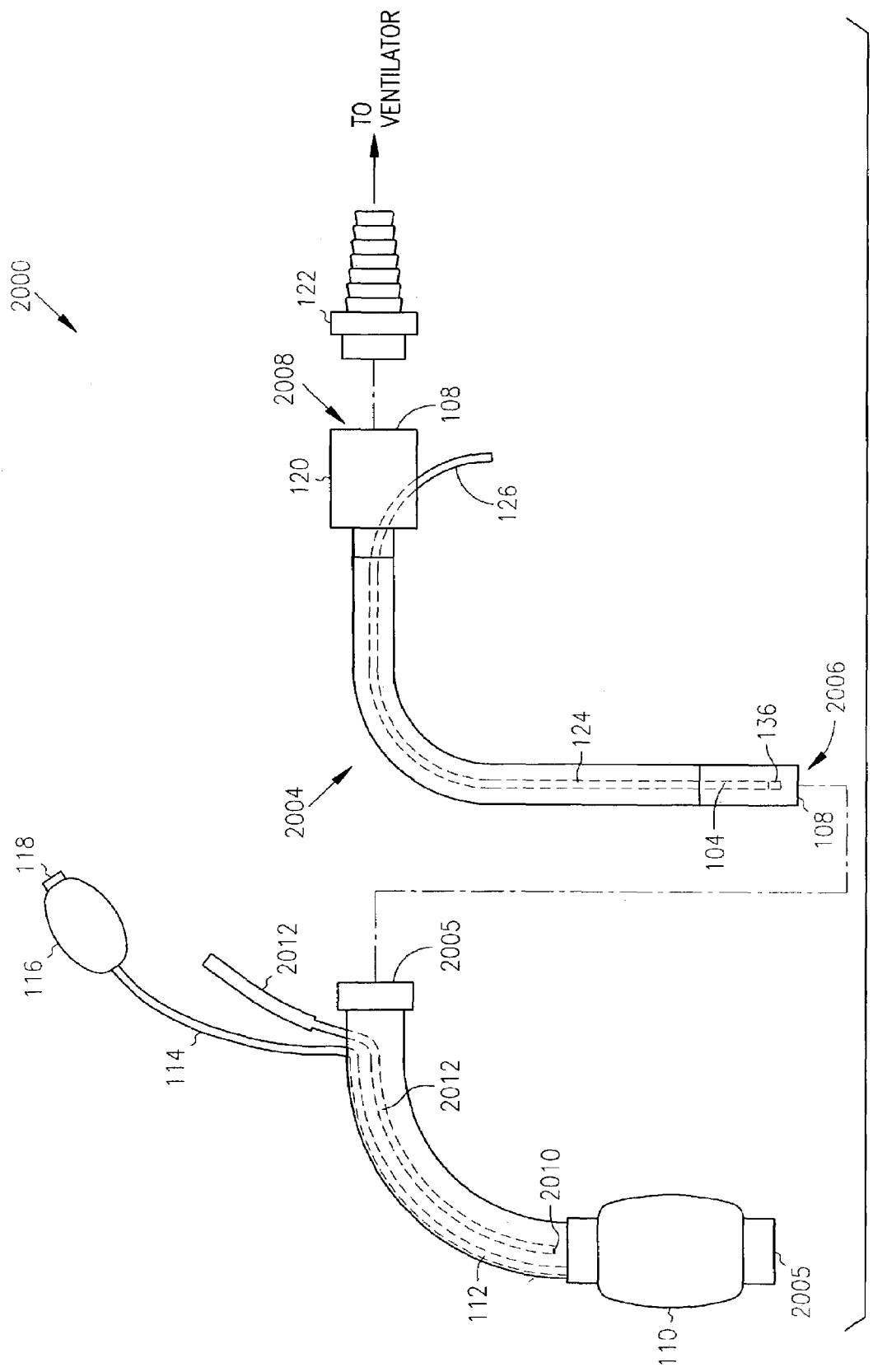
FIG. 20 is an exploded side perspective view illustrating one example of a two-piece tracheal tube assembly.

FIG. 20 is an exploded side perspective view illustrating generally, by way of example, but not by way of limitation, one embodiment of a two-piece tracheal tube assembly 2000. In this example, two-piece tracheal tube assembly 2000 includes two tubes, such as an outer cannula 2002 and an inner cannula 2004. Outer cannula 2002 includes inflatable cuff 110, located at or near its distal end for providing a seal between outer cannula 2002 and an inner diameter of the patient's trachea, i.e., tracheal wall 202. For inflating cuff 110, cuff lumen 112 extends from cuff 110 to a proximal end of outer cannula 2002, and cuff tube 114 extends, in fluid communication therewith, outwardly from the proximal end of outer cannula 2002, such as toward cuff pressure bladder 116 and inflation port 118, or the like. In this example, outer cannula 2002 includes a lumen 2005, extending from its distal end to its proximal end, for receiving inner cannula 2004 slid therethrough.

Inner cannula 2004 is sized and shaped to slide snugly into the proximal end of lumen 2005 of outer cannula 2002, such that, in one example, when completely inserted therein, a distal end 2006 of inner cannula 2004 extends beyond (more distal than) cuff 110. In one such example, distal end 2006 of inner cannula 2004 is inserted such that it is located at the distal end of outer cannula 2002. In one such example, distal end 2006 of inner cannula 2004 is inserted such that it is located beyond the distal end of outer cannula 2002. Inner cannula 2004 includes an air passage 108 extending between its distal end 2006 and its proximal end 2008.

In this example, distal end 2006 of inner cannula 2004 includes a fluid pickup assembly 104, such as discussed above or similar thereto. Fluid pickup assembly 104 includes at least one wicking fluid pickup port 136, as discussed above or similar thereto. Inner cannula 2004 includes at least one fluid removal lumen 124 extending longitudinally between one or more locations at or near its distal end 2006 and one or more locations at or near its proximal end 2008. In the example illustrated in FIG. 20, fluid removal lumen 124 extends to coupling stem 126, and is in fluid communication therewith. Coupling stem 126 is sized and shaped to be coupled in fluid communication with a fluid removal tube 128, such as illustrated in FIG. 1, and which, in turn, is coupled to a pump assembly 106. Fluid removal lumen 124 provides fluid communication between the at least one fluid pickup port 136 and coupling stem 126. In one example, at least a portion of the at least one fluid removal lumen 124 is integrally formed with inner cannula 2004, for example, by extending longitudinally within a wall of inner cannula 2004. In another example, at least a portion of the at least one fluid removal lumen 124 is glued or otherwise affixed to and/or carried within, air passage 108, which extends longitudinally through inner cannula 2004. In a further example, at least a portion of the at least one fluid removal lumen 124 is glued or otherwise affixed to an outer wall of inner cannula 2004. In yet a further example, the at least one fluid removal lumen 124 is implemented as a removable tube that is inserted through air passage 108, or through a sleeve or other guide structure extending longitudinally along one of the inner cannula 2004 or the outer cannula 2002.

In one example, outer cannula 2002 is the outer cannula of a commercially-available two-piece tracheal tube assembly having outer and inner cannulas. In this example, inner cannula 2004 is sized and shaped for being substituted for the inner cannula of the commercially available two-piece tracheal assembly, that is, inserted into its outer cannula to provide at least one wicking fluid pickup port 136 located below (more distal than) cuff 110.

In another example, outer cannula 2002 includes a wicking or non-wicking fluid pickup port 2010 located toward the distal end of outer cannula 2002, but above (more proximal than) cuff 110. Fluid pickup port 2010 is coupled by a fluid removal lumen 2012 to pump 132, or to a different pump. In one example, such as where fluid pickup port 2010 is non-wicking, it is coupled to a suctioning pump that does use airflow to assist in removing fluid. This does not interfere with ventilation of the patient, because, such an airflow-assisted suctioning pump applies airflow-assisted suction at a location above cuff 110, which blocks passage of such air to the patient's lungs.

In one example, inner cannula 2004 is long enough such that, when inserted through lumen 2005, distal end 2006 is located at or near that portion of trachea 200 that branches into separate bronchial tubes, or is located within one of the patient's bronchial tubes. This, in turn, positions the at least one wicking fluid pickup port 136 deep in trachea 200 or a bronchial tube (or both, such as for multiple fluid pickup ports 136). Removing fluid at such one or more such locations further enhances ventilation of the patient. In another example (such as where the fluid removal lumen 124 is implemented as a removable tube, as discussed above), a removable tube providing fluid removal lumen 124 extends beyond the ends of inner cannula 2004 and outer cannula 2002 for providing at least one more distal wicking fluid removal port 136.

Figure 21:
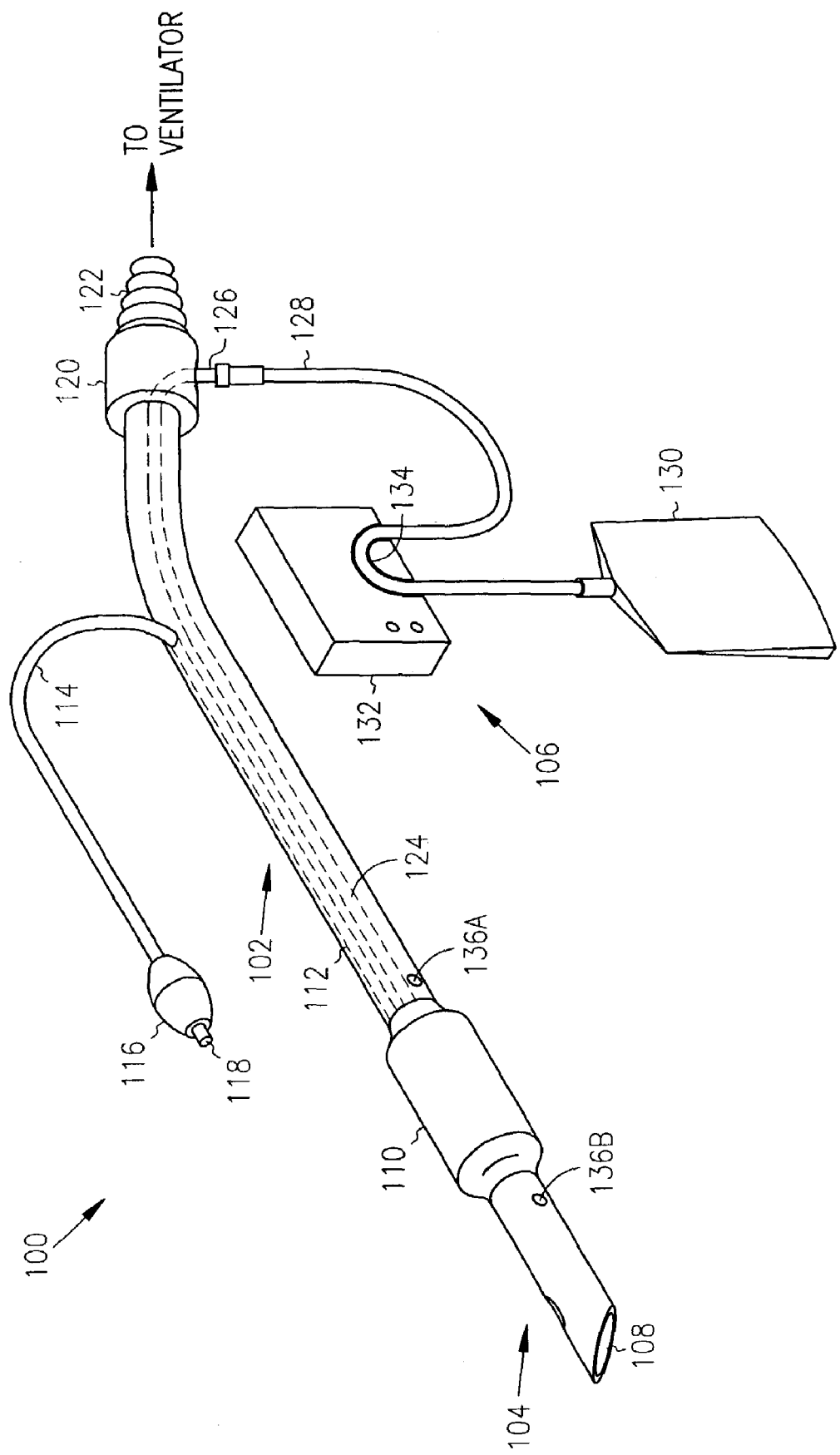
FIG. 21 is a perspective view, similar to FIG. 1, illustrating one example of a system including at least one wicking fluid pickup port located below a cuff and at least one wicking fluid pickup port located above the cuff.

FIG. 21 is a perspective view, similar in many respects to FIG. 1, illustrating generally, by way of example, but not by way of limitation, one embodiment of a system 100 including at least one wicking fluid pickup port 136A located below (more distal than) cuff 110 and at least one wicking fluid pickup port 136B located just above (more proximal than) cuff 110. In this example, wicking fluid pickup ports 136A–B are each coupled in fluid communication with a shared fluid removal lumen 124, coupling stem 126, and fluid removal tube 128. However, in an alternative example, wicking fluid pickup ports 136A–B are separately individually coupled to one or more of such components.

Figure 22:
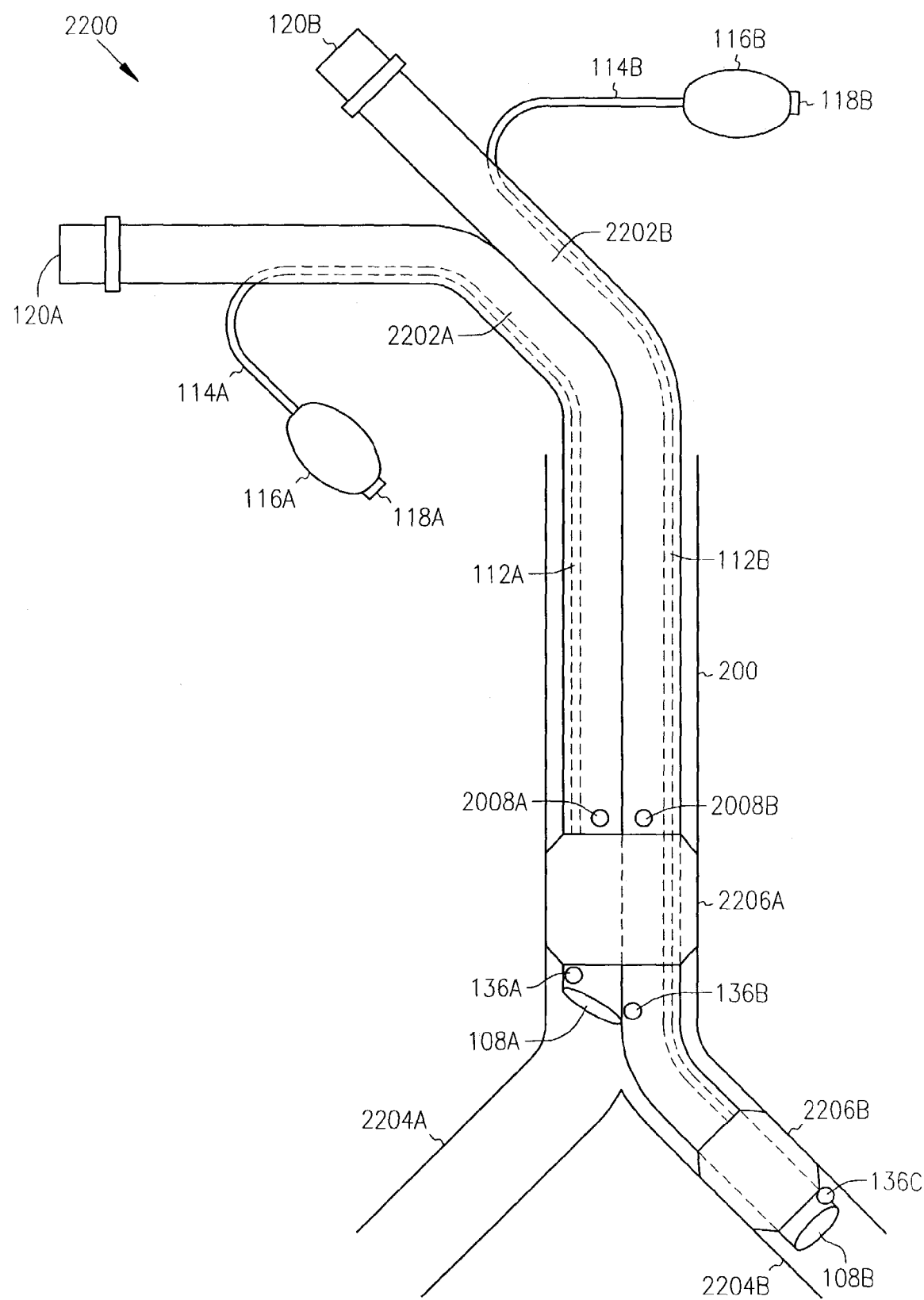
FIG. 22 is a side perspective view illustrating one example of a double-lumen tracheal tube including at least one wicking fluid pickup port.

FIG. 22 is a side perspective view illustrating generally, by way of example, but not by way of limitation, one embodiment of a double-lumen tracheal tube 2200 including at least one wicking fluid pickup port. In this example, tracheal tube 2200 includes tubes 2202A–B, intermediate portions of which are molded together or otherwise attached, such as illustrated in FIG. 22. Tube 2202A is sized such that its distal end terminates in the patient's trachea 200 when inserted therein. Tube 2202B is sized longer than tube 2202A, such that the distal end of tube 2202B extends into one of the patient's bronchial tubes 2204A–B when inserted therein. Inflatable cuff 2206A is located with trachea 200 near the distal end of tube 2202A. Inflatable cuff 2206A extends circumferentially about both tubes 2206A–B. When inflated, cuff 2206A provides a seal that prevents airflow outside of tubes 2206A–B and within trachea 200. Inflatable cuff 2206B is located within bronchial tube 2204B near the distal end of tube 220. Inflatable cuff 2206B extends circumferentially about tube 2202B. When inflated, cuff 2206B provides a seal that prevents airflow outside of tube 2202B and within bronchial tube 2204B. Cuffs 2206A–B are respectively coupled to corresponding cuff lumens 112A–B, cuff tubes 114A–B, cuff pressure bladders 116A–B, and inflation ports 118A–B, for inflating/deflating cuffs 2206A–B, such as discussed above. End couplers 120A–B are located at respective proximal ends of tubes 2202A–B for coupling either or both of the air passages 108A–B of tubes 2202A–B to the ventilator, or optionally blocking the same to obstruct airflow therethrough. Dual lumen tracheal tube 2200 allows ventilation of both lungs, or ventilation of one lung (with the other lung collapsed) by blocking the proximal end of that one of tubes 2202A–B that has its one of air passages 108A–B in fluid communication with the particular lung to be collapsed.

In this example, tracheal tube 2200 includes at least one wicking fluid pickup port 136 located below (more distal than) at least one of cuffs 2206A–B. In one example, at least one wicking fluid pickup port is located below cuff 2206A and above cuff 2206B, such as illustrated by wicking fluid pickup ports 136A–B. In another example, at least one wicking fluid pickup port is additionally or alternatively located below cuff 2206B, such as illustrated by wicking fluid pickup port 136C. In a further example, at least one wicking or non-wicking fluid pickup port is additionally located above cuff 2206A, such as illustrated by wicking or non-wicking fluid pickup port 2008A and/or 2008B. Fluid that is introduced into one of the wicking fluid pickup ports illustrated in FIG. 22 is removed using integral or separately formed fluid removal lumens and/or tubes coupled to at least one pump assembly, such as discussed above or similar thereto. Although FIG. 22 illustrates wicking fluid pickup ports located on portions of lumens 2202A–B, it is understood that wicking fluid pickup ports 136A and/or 136C, for example, may alternatively be implemented on a distal portion of a tube passed through an air passage 108A–B of a respective one of tubes 2202A–B, such as discussed above or similar thereto.

Figure 23:
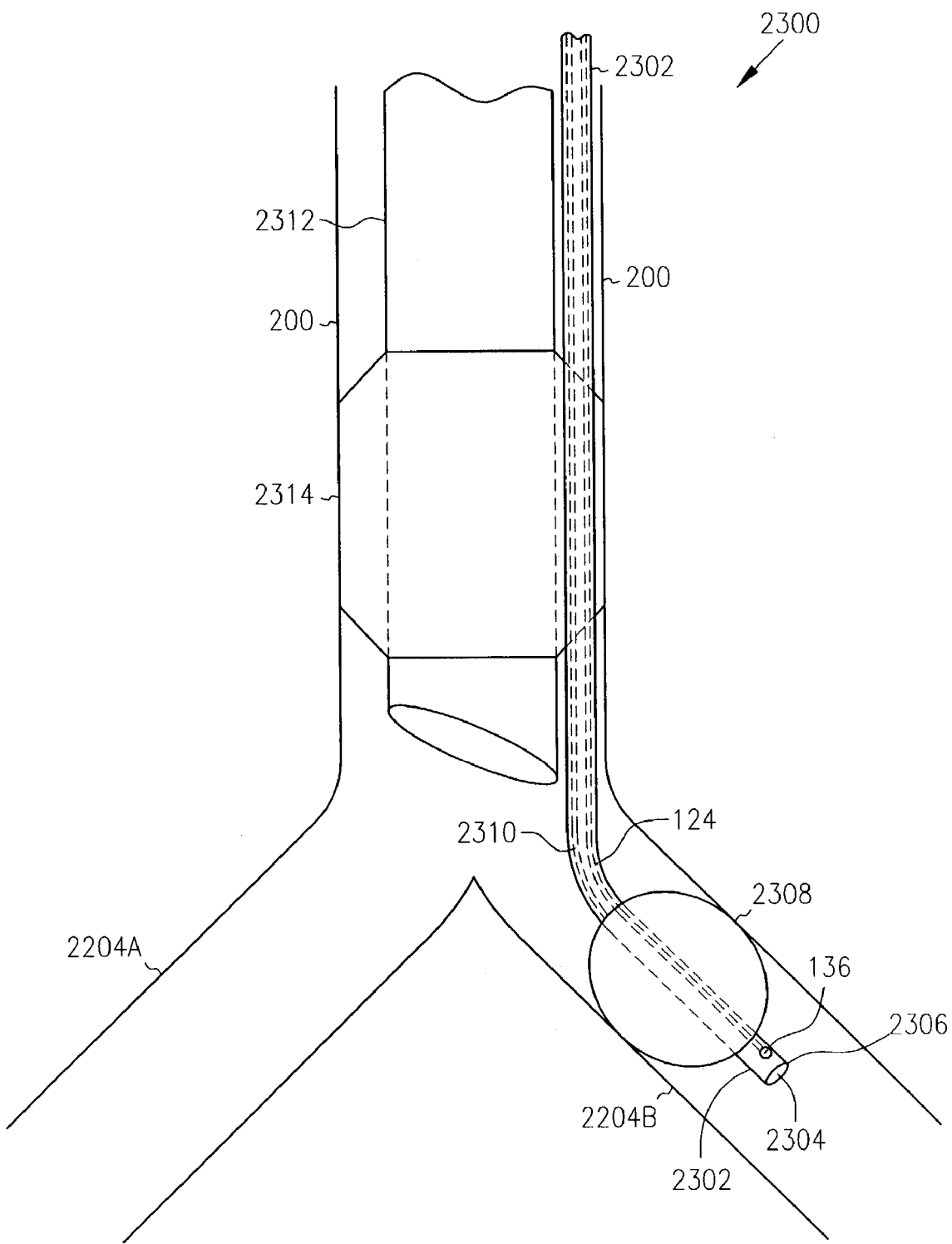
FIG. 23 is a side perspective view illustrating one example of a bronchial blocker assembly including at least one wicking fluid pickup port.

FIG. 23 is a side perspective view illustrating generally, by way of example, but not by way of limitation, one embodiment of a bronchial blocker assembly 2300 including at least one wicking fluid pickup port 136. In this example, bronchial blocker assembly 2300 includes an elongated catheter 2302. Catheter 2302 is sized and shaped such that it can be introduced within trachea 200 and into a desired one of the patient's bronchial tubes 2204A–B. In one example, catheter 2302 includes a center lumen 2304 extending longitudinally from a distal end 2306 of catheter 2302 to a proximal end of catheter 2302. Center lumen 2304 is sized and shaped such that catheter 2302 is capable of being received over a guidewire or stylet that introduces and guides catheter 2302 to the desired location within the selected one of the patient's bronchial tubes 2204A–B. Bronchial blocker 2300 includes an inflatable cuff 2308 located at or near its distal end 2306. For inflating cuff 2308, a cuff lumen 2310 extends longitudinally, in fluid communication from cuff 2308, toward a proximal end of bronchial blocker 2300.

When inflated, cuff 2308 blocks airflow through the selected bronchial tube 2204B except through center lumen 2304. However, bronchial blocker 2300 also includes, at its proximal end, a plug for obstructing center lumen 2304 when cuff 2308 is inflated. Therefore, by inflating cuff 2308 and plugging center lumen 2304, bronchial blocker 2300 blocks airflow to the selected one of the patient's lungs by obstructing the corresponding bronchial tube 2204B. In this example, bronchial blocker assembly 2300 also includes at least one wicking fluid pickup port 136 located below (more distal than) cuff 2308. At least one corresponding fluid removal lumen 124 is connected in fluid communication with the at least one wicking fluid pickup port 136. In one example, fluid removal lumen 124 is formed integrally with catheter 2302 (e.g., extending longitudinally within its sidewall). In another example, the at least one fluid removal lumen 124 is implemented as a separate tube (e.g., extending longitudinally within or outside of catheter 2302). Fluid removal lumen 124 extends longitudinally toward a proximal end of bronchial blocker assembly 2300, where it is coupled to a pump assembly 106, such as by using a coupling stem 126 and fluid removal tube 128 as described above, or a similar technique.

In the example illustrated in FIG. 23, bronchial blocker assembly 2300 is used in conjunction with a tracheal tube assembly 2312 located in the patient's trachea 200. Bronchial blocker 2300 blocks ventilation of one lung, while tracheal tube assembly 2312 ventilates the other lung after inflation of its cuff 2314 to occlude trachea 200. In the example illustrated in FIG. 23, bronchial blocker assembly 2300 is disposed within trachea 200 adjacent to tracheal tube assembly 2312. However, in an alternative example, bronchial blocker assembly 2300 is inserted through center lumen air passage 2316 of tracheal tube assembly 2300. In such an example, separate couplings provided at the proximal end of tracheal tube assembly 2300 for introducing bronchial blocker 2300 and for coupling air passage 2316 to the mechanical ventilator.

OTHER APPLICATIONS

Figure 24:
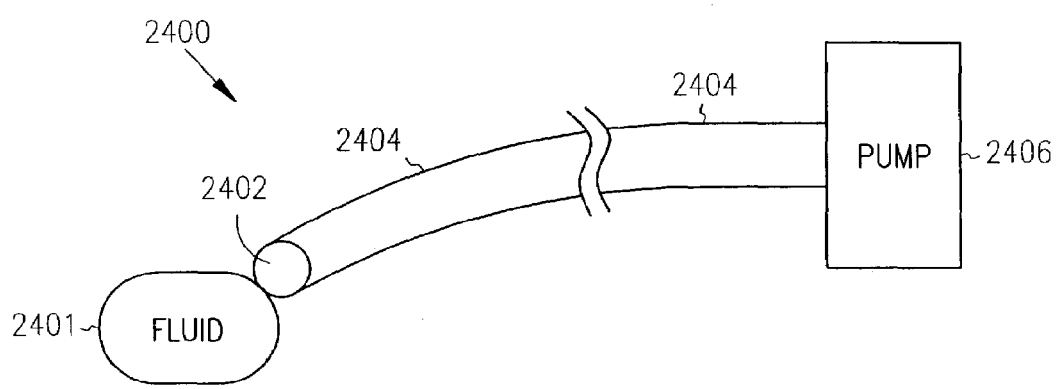
FIG. 24 is a schematic diagram illustrating generally one example of a generalized system using surface energy assistance in transporting and/or separating a fluid.

FIG. 24 is a schematic diagram illustrating generally, by way of example, but not by way of limitation, a generalized system 2400 using surface energy assistance in transporting and/or separating a fluid 2401. In this example, system 2400 includes at least one wicking fluid pickup port 2402 in fluid communication with at least one lumen, tube, or other fluid conduit 2404, which, in turn, is in fluid communication with a pump 2406. In certain respects, system 2400 operates similarly to the system 100, described above. However, system 2400 illustrates conceptually some more generalized useful applications.

In one example, system 2400 is used for separating first and second constituent fluid components of a nonhomogeneous fluid 2401. The wicking fluid pickup port 2402 is tailored (e.g., by sizing and/or shaping and/or selecting the surface energy affecting material properties of the port) to promote wicking-in of the first constituent fluid component of fluid 2401 and/or to avoid wicking-in of the second constituent fluid component of fluid 2401, such as discussed above. In this example, the first constituent fluid component of fluid 2401 is urged by pump 2406 through fluid conduit 2404 toward a holding receptacle or toward a different location, such as discussed above.

One suitable fluid separation example is for cleaning up a fuel (e.g., oil, gasoline, etc.) spill into a body of water. In this example, wicking fluid pickup port 2402 is tailored to promote wicking-in of the spilled fuel to separate it from the water. In another example, wicking fluid pickup port 2402 is tailored to promote wicking-in of a specific bodily fluid, such as for assisting in wound drainage. System 2400 and its wicking fluid pickup port 2402 can be used in variety of medical, industrial, or other processes for providing surface-energy assisted fluid transportation and/or separation. In one example, system 2400 is used in an agricultural process for separating different constituents of liquid animal digestive wastes, e.g., in a manure containment structure.

System 2400 can also be combined with a variety of other apparatuses. In one such example, system 2400 provides surface-energy assisted removal of oil or other fluid 2401 that has collected in a drip pan on an engine or other machine. In a somewhat different example, system 2400 uses surface-energy to wick-in a lubricant from a reservoir and to deliver the lubricant to a mechanical component (e.g., a drill bit) needing lubrication.

Figure 25:
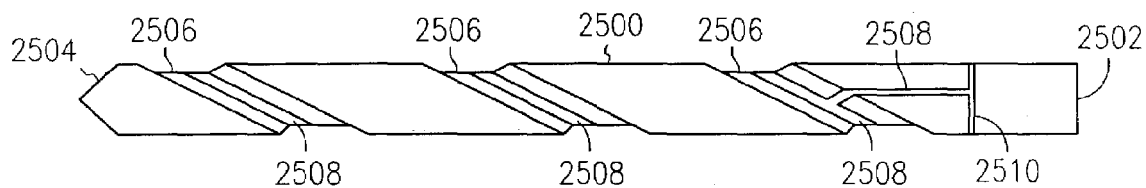
FIG. 25 is a schematic diagram illustrating generally one example of a drill bit including a wicking channel, such as for transporting a lubricant.

FIG. 25 is a schematic diagram illustrating generally one example of a substantially cylindrical drill bit 2500 including a proximal end 2502, a pointed distal end 2504, and a cutting groove or channel 2506 spiraling circumferentially therebetween. This example also includes a lubricant-wicking conduit such as channel 2508 extending between locations at or near the proximal end 2502 and the distal end 2504, such as within the cutting channel 2506. The wicking channel 2508 is sized and/or shaped and/or selected of a material having a surface tension affecting characteristic that wicks a lubricant into and through the wicking channel 2508. In this example, lubricant is delivered to a lubricant-primed wicking channel 2508 (e.g., using system 2400, or by using any other technique) at or near the proximal end 2502 of the bit 2500. In one example, a sponge delivers the lubricant to a ring channel 2510, which extends circumferentially about the proximal end 2502 of the drill bit 2500, and from which wicking channel 2508 extends. The lubricant then wicks into and through wicking channel 2508 to the distal end 2504 of the bit 2500. This transports lubricant to the distal end 2504 of the bit 2500. The lubricant is removed from the distal end 2504 of the bit 2500, such as by the wiping against the material being drilled through. Such lubricant removal from the distal end 2504 of the bit 2500 can be conceptualized as a type of pumping that assists the wicking fluid transport.

Figure 26:
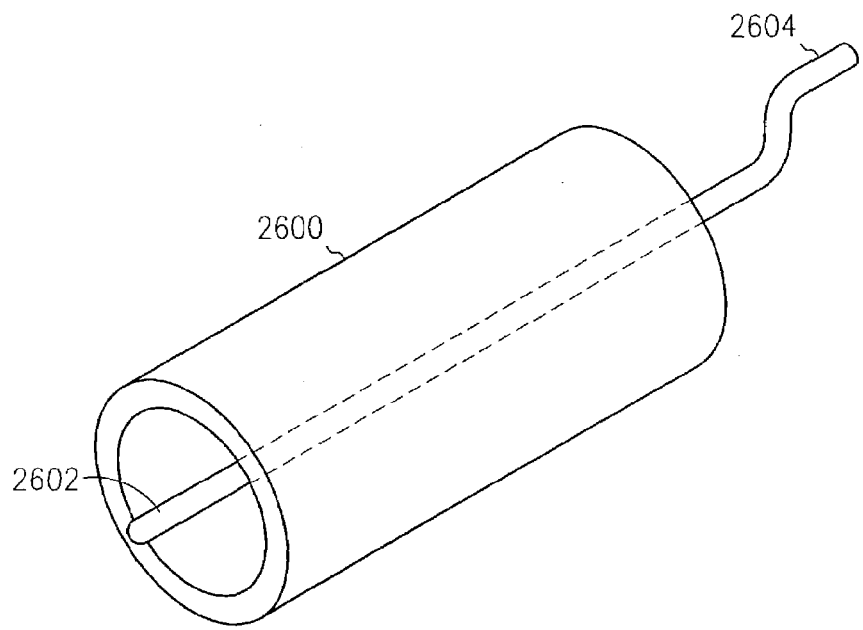
FIG. 26 is a schematic diagram illustrating an example of a liquid wicking channel in the interior portion of a conduit, and also illustrates one example of surface-energy assisted fluid transport across a boundary between regions having different pressures.

FIG. 26 is a schematic diagram illustrating another example in which at least one liquid wicking conduit such as wicking channel 2602 is implemented within the interior portion of a conduit such as a tube 2600. In one method of use, the tube 2600 is used to transport a gas, such as compressed air, that may generate a liquid condensate within the tube 2500. Wicking channel 2602 is used to transport such liquid. In one example, wicking channel 2602 is coupled in fluid communication with a fluid transport lumen such as a tube 2604, which is coupled to a pump, for providing further fluid transport, such as illustrated in FIG. 24, to a fluid holding receptacle or elsewhere. The tube 2604 is sized and/or shaped and/or made from a material such that the transported fluid bridges its interior diameter, as discussed above.

FIG. 26 also illustrates one example of surface-energy assisted fluid transport across a boundary between regions having different pressures. More particularly, in the example of FIG. 26 in which tube 2600 transports compressed air, the interior of tube 2600 is at high pressure and the exterior of tube 2600 is at lower pressure. Tube 2604, which provides bridging of the transported liquid across its interior diameter, thereby provides a convenient barrier for crossing the boundary between two regions at different pressures.

Returning to FIG. 24, in yet another example of the system 2400 extracts fluid 2401 from a solid-liquid mixture to solidify the mixture. For example, where a patient's colon has been removed, system 2400 can be used to wick-in and remove fluid to solidify the patient's digestive wastes. In another example, system 2400 is used in an agricultural process for solidifying animal digestive wastes, e.g., in a manure containment structure. Moreover, system 2400 need not operate at room or body temperature. System 2400 may instead operate at other temperatures. One such example is for fluid transportation and/or separation of substances that may not be in a liquid state at room or body temperatures. In one such example, system 2400 wicks-in, for separation and/or transportation, a molten constituent of a molten metal alloy that constitutes fluid 2401.

It is to be understood that the above description is intended to be illustrative, and not restrictive. For example, the above-described embodiments, or aspects thereof, may be used in combination with each other. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects.

What is claimed is:

1. A method comprising:
   inserting a tube into a subject's trachea;
   obstructing airflow at a first location outside of the tube and inside the trachea;
   ventilating at least one of the subject's lungs through the tube;
   wicking fluid, at a location that is proximal to the first location; and
   drawing the wicked fluid out of the subject,
   wherein the drawing the wicked fluid out of the subject comprises matching a flow rate at which the wicked fluid is drawn out of the subject to a mucus generation rate of the subject.

2. The method of claim 1, wherein the obstructing airflow comprises inflating a cuff.

3. The method of claim 1, wherein the drawing the wicked fluid out of the subject comprises using a peristalsis pump to provide a pressure for drawing the wicked fluid out of the subject.

4. The method of claim 1, further comprising storing the wicked fluid drawn out of the subject in a holding receptacle external to the subject.

5. The method of claim 1, further comprising directing mucus toward at least one wicking fluid pickup port.

6. The method of claim 1, further comprising limiting a pressure buildup, at a wicking fluid pickup port occluded by tissue.

7. A method comprising:
   inserting an outer cannula of a two-piece inflatable cuff tracheal tube into a subject's trachea;
   inflating the cuff to obstruct airflow between the outer cannula and the trachea;
   inserting an inner cannula of the two-piece inflatable cuff tracheal tube into the outer cannula;
   ventilating at least one of the subject's lungs through the inner cannula;
   wicking fluid, using a wicking fluid pickup portal carried by the inner cannula, at a location that is proximal to the cuff; and
   drawing the wicked fluid out of the subject,
   wherein the drawing the wicked fluid out of the subject comprises matching a flow rate at which the wicked fluid is drawn out of the subject to a mucus generation rate of the subject.

8. The method of claim 7, wherein the drawing the wicked fluid out of the subject comprises drawing a substantially contiguous liquid column through a lumen using a peristalsis pump, and further comprising storing the wicked fluid drawn out of the subject in a holding receptacle external to the subject.

9. A method comprising:
inserting a tube into a subject's trachea;
obstructing airflow at a first location outside of the tube and inside the trachea;
ventilating at least one of the subject's lungs through the tube;
wicking fluid, at a location that is distal to the first location; and
drawing the wicked fluid out of the subject,
wherein the drawing the wicked fluid out of the subject comprises matching a flow rate at which the wicked fluid is drawn out of the subject to a mucus generation rate of the subject.

10. The method of claim 9, wherein the obstructing airflow comprises inflating a cuff.

11. The method of claim 9, wherein the drawing the wicked fluid out of the subject comprises using a peristalsis pump to provide a pressure for drawing the wicked fluid out of the subject.

12. The method of claim 9, further comprising storing the wicked fluid drawn out of the subject in a holding receptacle external to the subject.

13. The method of claim 9, further comprising directing mucus toward at least one wicking fluid pickup port.

14. The method of claim 9, further comprising limiting a pressure buildup, at a wicking fluid pickup port occluded by tissue.

15. A method comprising:
inserting an outer cannula of a two-piece inflatable cuff tracheal tube into a subject's trachea;
inflating the cuff to obstruct airflow between the outer cannula and the trachea;
inserting an inner cannula of the two-piece inflatable cuff tracheal tube into the outer cannula;
ventilating at least one of the subject's lungs through the inner cannula;
wicking fluid, using a wicking fluid pickup portal carried by the inner cannula, at a location that is distal to the cuff; and
drawing the wicked fluid out of the subject,
wherein the drawing the wicked fluid out of the subject comprises matching a flow rate at which the wicked fluid is drawn out of the subject to a mucus generation rate of the subject.

16. The method of claim 15, wherein the drawing the wicked fluid out of the subject comprises drawing a substantially contiguous liquid column through a lumen using a peristalsis pump, and further comprising storing the wicked fluid drawn out of the subject in a holding receptacle external to the subject.

* * * * *